United States Patent [19]
Rieu et al.

[11] Patent Number: 6,011,032
[45] Date of Patent: Jan. 4, 2000

[54] HETEROCYCLIC COMPOUNDS FOR TREATING MYOCARDIAL ISCHEMIA

[75] Inventors: Jean-Pierre Rieu; Jean-François Patoiseau, both of Castres; Gareth W. John, Les Salvages; Bruno Legrand, Lautrec; Jean-Pierre Valentin, Revel, all of France

[73] Assignee: Pierre Fabre Medicament, Boulogne, France

[21] Appl. No.: 09/011,207

[22] PCT Filed: Jul. 25, 1996

[86] PCT No.: PCT/FR96/01176

§ 371 Date: Jan. 26, 1998

§ 102(e) Date: Jan. 26, 1998

[87] PCT Pub. No.: WO97/05134

PCT Pub. Date: Feb. 13, 1997

[30] Foreign Application Priority Data

Jul. 26, 1995 [FR] France .................. 95 09079

[51] Int. Cl.[7] ................. A61K 31/54; A61K 31/535; C07D 279/16; C07D 265/12
[52] U.S. Cl. ............ 514/224.2; 514/211; 514/230.5; 540/552; 544/50; 544/90
[58] Field of Search ................ 514/211, 224.2, 514/230.5; 540/552; 544/50, 90

[56] References Cited

FOREIGN PATENT DOCUMENTS 0 184 257  11/1986  European Pat. Off. .......... 413/12

*Primary Examiner*—Richard L. Raymond
*Assistant Examiner*—Brenda Coleman
*Attorney, Agent, or Firm*—The Firm of Gordon W. Hueschen

[57] ABSTRACT

Substituted N-heterocyclyl-1-aryloxyalkyl-4-piperldineamines of formula (I)

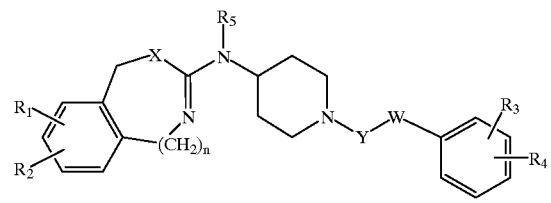

wherein each of $R_1$ to $R_4$, which are the same or different, is hydrogen, optionally branched $C_{1-4}$ alkyl, optionally branched $C_{1-4}$ alkyloxy, halo, nitro, hydroxy, or trifluoromethyl or trifluoromethoxyl; $R_5$ is hydrogen, optionally branched $C_{1-6}$ alkyl, optionally branched $C_{7-12}$ phenylalkyl optionally substituted on the phenyl by one or more radicals having the same definition as $R_1$; W and X are oxygen or sulphur; Y is $C_{2-6}$ polymethylene or —$CH_2$—CH(OH)—$CH_2$—; and n is 0 or 1; and pure R or S isomers of said compounds, where applicable, as well as mixtures thereof, as well as therapeutically-acceptable organic or inorganic salts and hydrates of the compounds and a method for preparing the compounds and their use as drugs are all disclosed.

13 Claims, No Drawings

HETEROCYCLIC COMPOUNDS FOR TREATING MYOCARDIAL ISCHEMIA

The present application is a U.S. National Application filed under 35 USC 371 of PCT/FR96/01176, filed Jul. 25, 1996, based upon French application Serial No. 95.09079 filed July 26, 1995.

Coronary diseases constitute the prime cause of death in the western world. Myocardial ischemia has a highly complex etiology and is treated only with drugs that act indirectly. The derivatives currently used in myocardial infarction and angina are beta-blockers, nitro derivatives and calcium inhibitors which all act indirectly by a hemodynamic phenomenon.

However, it is accepted that the metabolites produced very early in ischemia (phospholipid catabolism and glycolysis) interfere with the inactivation of the sodium current. This inactivation generates, via the sodium/calcium exchanger in myocytes, an excess calcium charge (Kohlhardt M. et al. (1989) *FASEB J.* 3 pp. 1963–7 and Undrovinas A.I. et al. (1991) *Circulation Research* 71 pp. 1231–41). This final excess calcium charge induces contraction of the myocyte.

Recently, novel compounds with no appreciable hemodynamic effect and which act on the excess sodium charge have been claimed (Massingham R., John G. W. and Van Zwieten, *Drugs of Today* (1991) 27 (8), pp. 459–77) by the Janssen laboratories (E. Boddeke et al., TIPS (1987) 10 pp. 397–400; Ver Donck L., Borgers M., Verdonk F., *Cardiovascular Research* (1993) 27 pp. 349–357, patent EP 0,184,257) and Syntex (Patmore L. et al. *Br J Pharmacol* (1991) 104 suppl. 175 P; Alps B. J., *Br J Clin Pharmacol* (1992) 34 199–206 and U.S. Pat. No. 4,829,065.

In patent EP 0,184,257 representing the closest prior art, the products claimed consist partly of N-(2-benzothiazolyl-1-(phenoxyalkyl)-4-piperidinamine derivatives in which the leader products are R 56865 and Sabeluzole of formula:

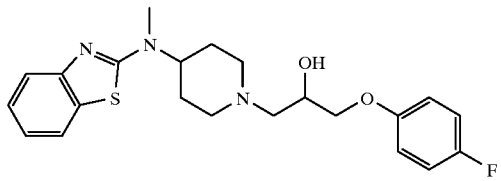

SABELUZOLE

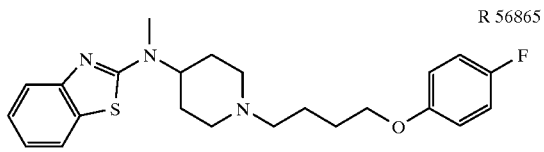

R 56865

MOLECULES CLAIMED

The molecules of the present invention belong to the class of N-substituted 1-(phenoxyalkyl)-4-piperidinamines of formula I:

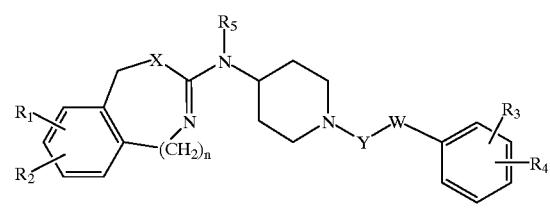

(I)

in which
R$_1$ to R$_4$, which may be identical or different, represent:
  a hydrogen
  a branched or unbranched alkyl containing from 1 to 4 carbon atoms
  a branched or unbranched alkyloxy containing from 1 to 4 carbon atoms
  a halogen group
  a nitro group
  a hydroxyl group
  a trifluoromethyl or trifluoromethoxy group,
R$_5$ represents:
  a hydrogen
  a branched or unbranched alkyl containing from 1 to 6 carbon atoms
  a branched or unbranched phenylalkyl containing from 7 to 12 carbons, which can be substituted on the aromatic with one or two radicals defined as R$_1$,
W and X represent:
  an oxygen or a sulfur,
Y represents:
  a polymethylene group containing from 2 to 6 carbon atoms
  the —CH$_2$—CH(OH)—CH$_2$— radical
n can take the values 0 or 1.

The invention also relates—when they exist—both to the pure R or S isomers and to mixtures thereof.

The present invention includes the therapeutically acceptable inorganic or organic salts of the compounds of general formula I and the possible hydrates thereof.

The invention also relates to the process for the preparation of the compounds claimed, as well as to their application as drugs.

The molecules of the present invention have potentially considerable cytoprotective properties on the heart or neurons, these properties generally being superior to those of the controls R 56865 and sabeluzole mentioned above.

SYNTHESIS OF THE COMPOUNDS OF FORMULA I

Depending on the size of the rings, one or more approaches may be envisaged for the synthesis of the compounds I.
A) Synthesis of the 6-membered derivatives:
Two routes of access are used to prepare the benzo(xa or thia)zines: indeed, it is possible to start with substituted 2-(halomethyl)phenyliso(thio)cyanates or 4-piperidyliso(thio)cyanates—substituted in position 1.
1°) Preparation starting with 2-(bromo or chloro methyl)-phenyliso(thio)cyanates:
  (cf. Synthetic Scheme I)
  These compounds (II) are prepared by substitutive radical halogenation of suitably substituted o-tolyliso(thio)-cyanates (cf. J. Gonda and P. Kristian *Collect Czech Chem*

*Commun* (1986) 51 pp. 2802–9; J. Gonda and M. Barnikol *Collect Czech Chem Commun* (1990) 55 pp. 752–60 and E. Klauke and L. Oehlmann, *Synthesis* (1978) pp. 376–7). The 4-piperidinamines (III) used can be substituted in position 1 either with the radical ($R_3$, $R_4$—$C_6H_3$—W—Y—) of the present invention (cf. A. M. Ismaiel et al. *J Med Chem* (1993) 36 pp. 2519–25) or protected in the form of the benzyl derivative (G. C. Caïn *Bioorg Med Chem Letters* (1994), 4, pp. 329–34) or in the form of the ethyl carbamate. The condensation between the 2 molecules (II, III) is carried out according to Gonda and P. Kristian; Gonda and Barnikol already mentioned or W. Gauss and H. J. Kabbe, *Synthesis* (1978) pp. 377–9, and leads:

either to the expected derivative I or to the blocked piperidine (IV) whose deblocking is carried out according to Bingwei V. Yang et al., *Synlett* (1993), pp. 195–6, or by acidic hydrolysis to give the free amine (V). This can be condensed either with the ω-bromoalkyl phenyl ether (IV) (prepared according to A. M. Ismaiel et al., already mentioned) or with an aryl glycidyl ether (VII) (prepared according to W. S. Di Menna et al., *J. Med. Chem.* (1978) 21, pp. 1073–1076, to give the expected suitably substituted derivative I.

SYNTHETIC SCHEME I:

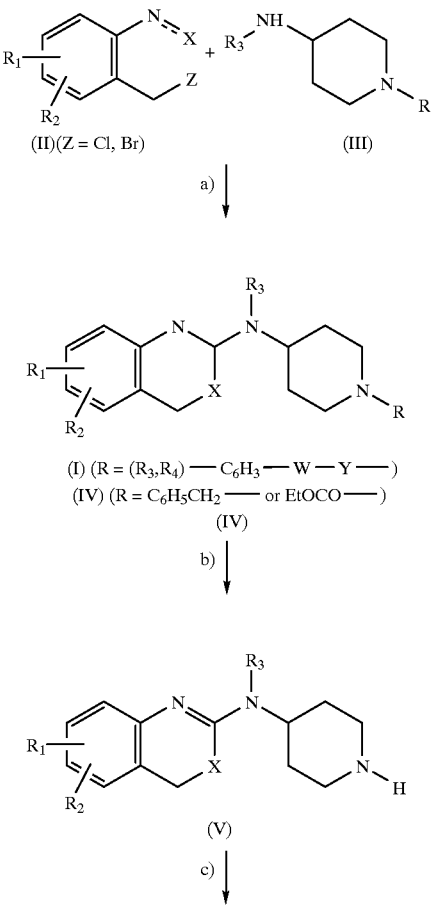

2°) Preparation starting with 1-substituted 4-piperidyliso (thio)cyanates (IX):

(Synthetic Scheme II).

When the iso (thio)cyanates (II) are difficult to prepare, it is preferable to start with 4-piperidyliso(thio)-cyanates (IX). These iso(thio)cyanates IX used are prepared from the amines III previously described either using triphosgene (H. Eckert and B. Foster, *Angew Chem Int Ed English* (1987) 26 pp. 894–5) or di-2-pyridyl thiocarbonate (S. Kim, K. Y. Yi *Tetrahedron Letters* (1985) 26 pp. 1661–4) or N,N'-thiocarbonyldiimidazole (Staab H. A. and G. Walther, Ann (1962) 657 104–107).

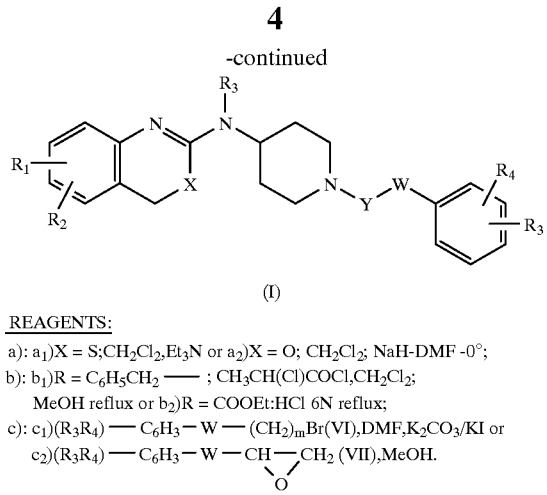

(I)

REAGENTS:

a): $a_1$)X = S;$CH_2Cl_2$,$Et_3N$ or $a_2$)X = O; $CH_2Cl_2$; NaH-DMF -0°;

b): $b_1$)R = $C_6H_5CH_2$—— ; $CH_3CH(Cl)COCl$,$CH_2Cl_2$;
  MeOH reflux or $b_2$)R = COOEt:HCl 6N reflux;

c): $c_1$)($R_3R_4$)——$C_6H_3$—W—($CH_2$)$_m$Br(VI),DMF,$K_2CO_3$/KI or
  $c_2$)($R_3R_4$)——$C_6H_3$—W—CH—$CH_2$ (VII),MeOH.
  \O/

SYNTHETIC SCHEME II:

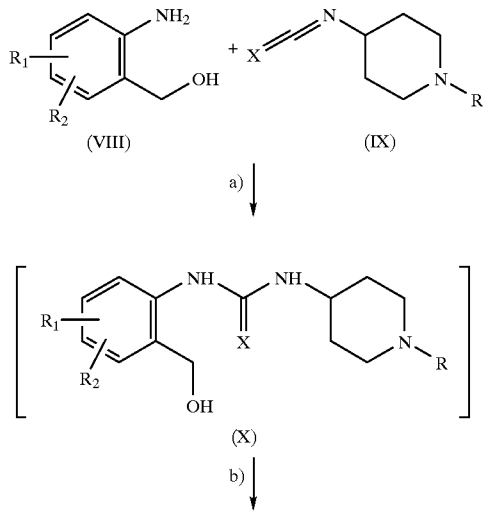

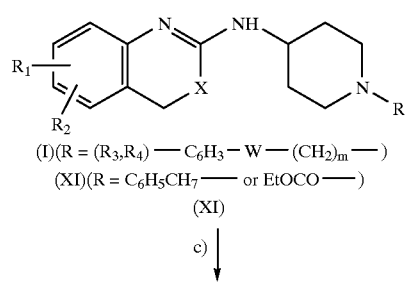

(I)(R = ($R_3$,$R_4$)——$C_6H_3$—W—($CH_2$)$_m$——)
(XI)(R = $C_6H_5CH_7$—— or EtOCO——)
(XI)

c)

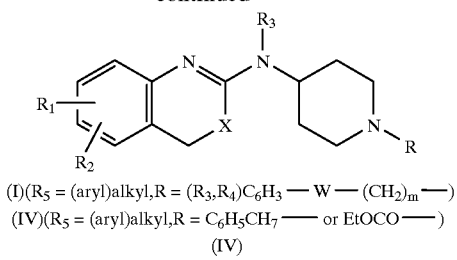

(I)(R₅ = (aryl)alkyl,R = (R₃,R₄)C₆H₃ — W — (CH₂)ₘ —)
(IV)(R₅ = (aryl)alkyl,R = C₆H₅CH₇ — or EtOCO —)
(IV)

d) ↓

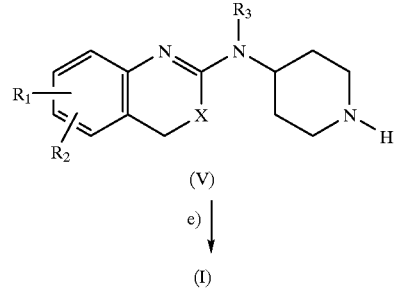

(V)

e) ↓

(I)

REAGENTS: a): Dioxane or THF;
b): conc. HCl; or Mitsunobu reaction;
c): DMF,NaH or K₂CO₃,R₅ — I or R₅ — Br;
d): Cf.b₁ or b₂ Scheme I;
e): Cf.c₁ or c₂ Scheme I.

These iso(thio)Cyantes are condensed with the 2-aminobenzyl alcohols (VIII) to give, in refluxing dioxane, intermediate o-hydroxymethylphenlureas (X) which, without being isolated, are cyclized in concentrated hydrochloric acid into the expected derivative (I) with R₅=H or in the form of the derivative (XI) N-protected with benzyl or ethyl carboxylate groups. The N-alkylation after sodation with NaH or Na₂CO₃ in DMF gives the compounds (I) and (IV) with R₅=(ar)alkyl. The deprotection of (IV) is then carried out as in Scheme I to give, finally, after N-alkylation, the suitably substituted compounds (I) of the present invention.

B) Synthesis of the 7-membered compounds:
(cf. Synthetic Scheme III)

SYNTHETIC SCHEME III:

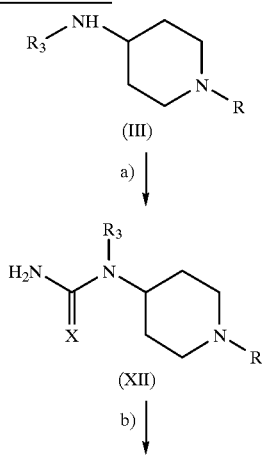

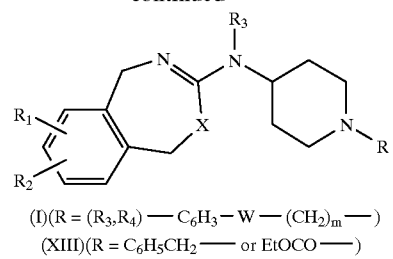

(I)(R = (R₃,R₄) — C₆H₃ — W — (CH₂)ₘ —)
(XIII)(R = C₆H₅CH₂ — or EtOCO —)
(XIII)

c) ↓

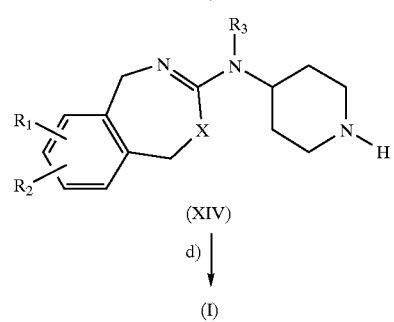

(XIV)

d) ↓

(I)

REAGENTS:
a): (CH₃)₃CCOCl,KXCN,CH₃COCH₃,25°; conc. HCl; 90°;
b): R₁ ⟨benzene ring with [ClBr] groups⟩ R₂ (XV),Na₂CO₃,CH₃COCH₃,reflux;
c): Cf.b₁ or b₂ Scheme I;
d): Cf.c₁ or c₂ Scheme I.

The secondary diamine (III) is converted into the N,N-disubstituted (thio)urea (XII) by the action of sodium iso (thio)cyanate in the presence of pivaloyl chloride according to the process described in patent EP 126,934.

The pivaloylurea obtained is not isolated but is hydrolyzed in the presence of refluxing HCl, into the urea (XII).

This (thio)urea is then condensed with an o-xylene α,α'-dihalide according to the method of D. N. Reinhoudt (*Recueil Trav Chim Pays Bas* (1973) 92 pp. 20–32) to give the 2,4-(thia or oxa)zepines claimed (I) or the N-protected compounds of formula (XIII), which give, by deprotection (according to Scheme I), the compound (XIV) which is N-alkylated into the expected derivative I (n=1).

In the following, all temperatures are in degrees Centigrade unless otherwise indicated.

EXAMPLE 1

N-Methyl-N-[1-[4-(4-fluorophenoxy)butyl]piperid-4-yl]-4H-3,1-benzothiazin-2-amine hydrogen maleate (1).

A solution of 500 mg (2.19 mmol) of ortho-bromomethylphenyl isothiocyanate (m.p.=42°) is treated with 900 mg (2.19 mmol) of 1-(4-(4-fluorophenoxy)butyl)-N-methyl-4-piperidinamine dihydrochloride (m.p.=216°) and 1.2 ml (8.8 mmol) of triethylamine. The mixture is then brought to 80° under a stream of nitrogen for one hour. After cooling to 25° the insoluble material is removed and rinsed with toluene and the mother liquors are evaporated to dryness on a rotary evaporator under vacuum. The residue is taken up in methylene chloride, washed with water and with brine and the organic phase is then dried over sodium sulfate. The pale yellow oil obtained after filtration is evaporated to dryness and purified by "flash chromatography", eluting with a 97.5 $CH_2Cl_2$/2.25 MeOH/ 0.25 $NH_4OH$ mixture, to give, after evaporation (m=810 mg, yield: 86%) of cream-colored oil which eventually crystallizes.

A solution of 220 mg of maleic acid in hot ethyl acetate is added to a solution of the above base in the same solvent, the product is then left to crystallize slowly at 25° and the crystals of salt formed are filtered off (m=900 mg; yield: 72%). The product is recrystallized from ethyl alcohol to obtain 675 mg (yield: 54%) of white crystals of formula 1:

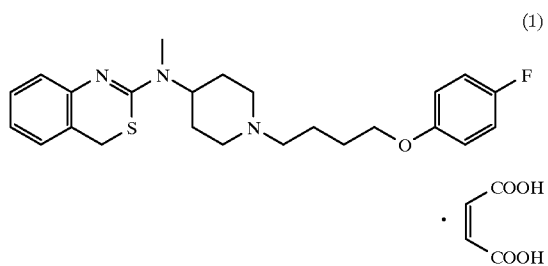

(1)

Empirical formula: $C_{28}H_{34}FN_3O_5S$; Molecular mass: 543.63; Melting point: 139–140°; IR (KBr): υ (C=N): 1618; $(COO^{31})$: 1586 $cm^{-1}$. NMR (DMSO $d_6$) δ: 1.6–2.3 (m, 8H), 3.01 (s, 3H); 3.1–3.8 (m, 6H); 3.95 (s, 2H); 3.8–4.2 (m, 2H); 4.5–4.9 (m, 1H); 6.02 (s, 2H); 6.8–7.05 (m, 4H); 7.05–7.3 (m, 4H); 8–11 (m, 2H).

EXAMPLE 2

N-Methyl-N-[1-[3-(4-fluorophenoxy)propyl]piperid-4-yl]-4H-3,1-benzothiazin-2-amine hydrogen maleate (2).

By condensing 500 mg (2.19 mmol) of ortho-bromomethylphenyl isothiocyanate with 745 mg (2.19 mmol) of N-methyl-1-[4-(4- fluorophenoxy)propyl]-4-piperidinamine dihydrochloride (m.p. >220°) according to the process described in Example 1, white crystals of formula 2 are obtained in a yield of 58%:

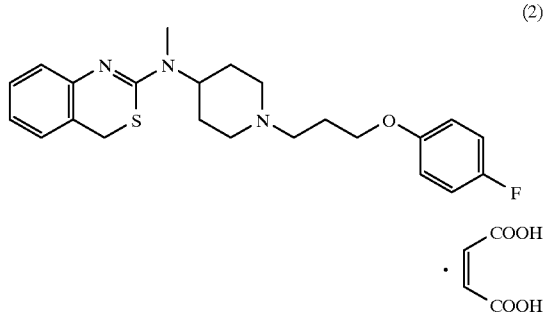

(2)

Empirical formula: $C_{27}H_{32}FN_3O_5S$; Molecular mass: 529.606; Melting point: 160–1610°IR (KBr): υ (N=C): 1610;$(COO^{31})$: 1540 $cm^{-1}$. NM (DMSO $d_6$) δ: 1.7–2.3 (m, 6H); 3.02 (s, 3H); 2.9–3.4 (m, 4H); 3.5–3.8 (m, 2H); 3.96 (s, 2H); 4.03 (t, 2H); 4.5–4.8 (m, 1H); 6.03 (s, 2H); 6.8–7.05 (m, 4H); 7.05–7.35 (m, 4H); 8.5–11 (m, 2H).

EXAMPLE 3

N-Methyl-N-[1-[2-(4-fluorophenoxy)ethyl]piperid-4-yl]-4H-3,1-benzothiazin-2-amine hydrogen maleate (3).

Working as described in Example 1, but starting with 856 mg of N-methyl-[1-[2-(4-fluorophenoxy)ethyl)-4-piperidinamine dihydrochloride (m.p.=241° C.), m=910 mg (yield: 68%) of white crystals of structure 3 are obtained:

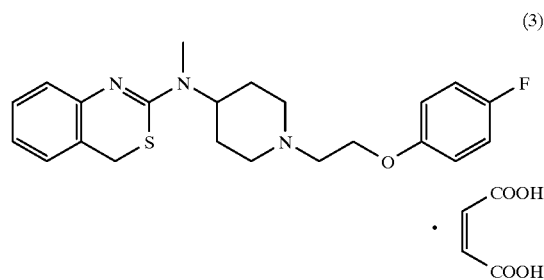

(3)

Empirical formula: $C_{26}H_{30}FN_3O_5S$; Molecular mass: 515.586; Melting point: 114–115° IR (KBr): υ (N=C): 1618; $(COO^{31})$: 1562 $cm^{-1}$. NMR ($CDCl_3$) δ: 2.01 (d, 2H); 2.3 (q.d, 2H); 2.85–3.2 (m, 2H); 3.11 (s, 3H); 3.44 (t, 2H); 3.45–3.9 (m, 2H); 3.89 (s, 2H); 4.33 (t, 2H); 4.8–5.2 (m, 1H); 6.3 (s, 2H); 6.75–6.92 (m, 2H); 6.95–7.15 (m, 5H); 7.2–7.35 (m, 1H); 8.5–11.5 (m, 2H).

EXAMPLE 4

N-[1-[4-(4-Fluorophenoxy)butyl]piperid-4-yl]-4H-3,1-benzothiazin-2-amine hydrogen maleate (4).

Using the procedure described in Example 1 and starting with 744 mg (2.19 mmol) of 1-[4-(4-fluorophenoxy)butyl]-4-piperidinamine dihydrochloride (m.p.=248°), 740 mg of expected base (m.p.=134°) are prepared, which product is then salified with maleic acid to give 880 mg (yield: 76%) of white crystals of formula 4:

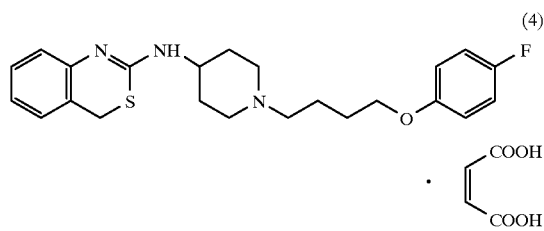

(4)

Empirical formula: $C_{27}H_{32}FN_3O_5S$; Molecular mass: 529.61; Melting point: 131–132° IR (KBr): υ (N=H): 3240; $(COO^{31})$: 1560 $cm^{-1}$. NMR (DMSO $d_6$) δ: 1.5–1.9 (m, 6H); 1.9–2.4 (m, 2H); 2.9–3.75 (m, 6H); 3.94 (s, 2H); 3.99 (t, 2H); 3.9–4.5 (m, 1H); 6.05 (s, 2H); 6.8–7.05 (m, 4H); 7.05–7.3 (m, 4H); 7.3–7.7 (m, 1H); 8.7–10.8 (m, 2H).

EXAMPLE 5

N-[1-[3-(4-Fluorophenoxy)propyl]piperid-4-yl]-4H-3,1-benzothiazin-2-amine hydrogen maleate monohydrate (5).

Using 713 mg (2.19 mmol) of 1-[3-(4-fluorophenoxy)-propyl]-4-piperidinamine dihydrochloride (m.p.=275–8°) and by condensing them with 500 mg (2.19 mmol) of ortho-bromomethylphenyl isothiocyanate according to the process described in Example 1, 560 mg (48% yield) of white crystals of formula 5 are prepared:

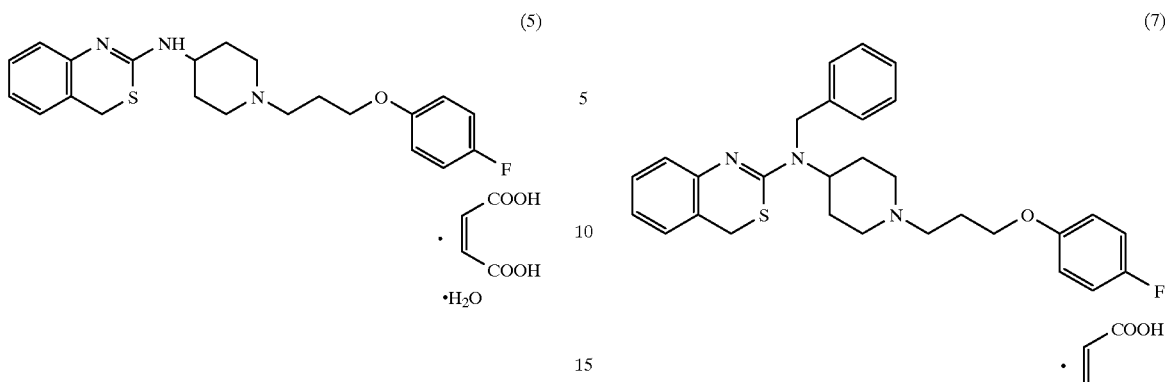

Empirical formula: $C_{26}H_{32}FN_3O_6S$; Molecular mass: 533.602; Melting point: 98–99°; IR (KBr): υ (OH): 3429; (N—H): 3256; ($COO^{31-}$): 1560 cm$^{-1}$. NMR (DMSO d$_6$) δ: 1.4–2.4 (m, 6H); 2.7–3.2 (m, 9H); 3.91 (s, 2H); 4.02 (t, 2H); 3.9–4.5 (m, 1H); 6.02 (s, 2H); 6.7–7 (m, 4H); 7–7.2 (m, 4H); 7.2–7.7 (m, 1H); 8.6–9.6 (m, 1H).

EXAMPLE 6

N-Ethyl-N-[1-[3 -(4-fluorophenoxy)propyl]piperid-4-yl]-4H-3,1-benzothiazin-2-amine hydrogen fumarate (6).

By adapting the process described in Example 1 to N-ethyl-N-[1-[3-(4-fluorophenoxy)propyl]-4-piperidinamine (m.p.=284°), 390 mg (yield: 33%) of beige-colored crystals of formula 6 are obtained:

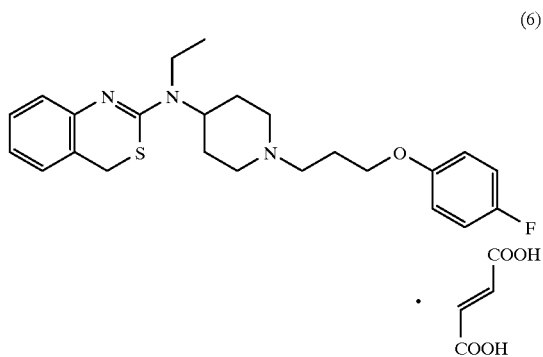

Empirical formula: $C_{28}H_{34}FN_3O_5S$; Molecular mass: 543.636; Melting point: 140–141°; IR (KBr): υ (COO$^-$): 1552 cm$^{-1}$. NMR (DMSO d$_6$) δ: 1.26 (t, 3H); 1.6–1.9 (m, 2H); 2–4 (m, 4H); 2.52 (t, 2H); 2.91 (t, 2H); 3.2–3.6 (m, 4H); 3.74 (s, 2H); 3.91 (t, 2H); 4.2–5.2 (m, 3H); 6.7 (s, 2H); 6.7–7.3 (m, 8H).

EXAMPLE 7

N-Benzyl-N-[1-[3-(4-fluorophenoxy)propyl]piperid-4-yl]-4H-3,1-benzothiazin-2-amine hydrogen maleate (7).

Using N-benzyl-1-[3-(4-fluorophenoxy)propyl]-4-piperidinamine dihydrochloride (m.p.=280°) (910 mg, 2.19 mmol) as starting material and reacting it according to the process of Example 1, 710 mg (yield: 53%) of white crystals of structure 7 are obtained:

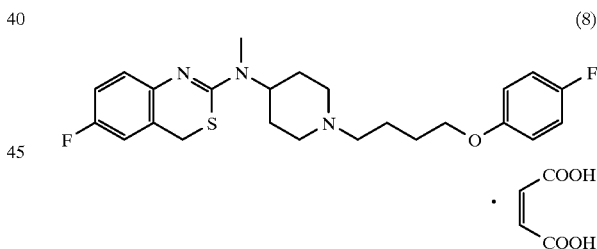

Empirical formula: $C_{33}H_{36}FN_3O_5S$; Molecular mass: 605.706; Melting point: 114–116°; IR (KBr): υ (N=C): 1601; ($COO^{31-}$): 1556 cm$^{-1}$. NMR (DMSO d$_6$) δ: 1.8–2.1 (m, 2H); 2.1–2.6 (m, 4H); 2.83 (t, 2H); 3.18 (t, 2H); 3.4–3.7 (m, 2H); 3.85 (s, 2H); 3.98 (t, 2H); 4.80 (s, 2H); 4.8–5.2 (m, 1H); 6.25 (s, 2H); 6.65–6.85 (m, 2H); 6.85–7.15 (m, 5H); 7.15–7.4 (m, 6H); 11.5–13.5 (m, 2H).

EXAMPLE 8

6-Fluoro-N-methyl-N-[1-4-(4-fluorophenoxy)butyl]piperid-4-yl]-4H-3,1-benzothiazin-2-amine hydrogen maleate (8).

Starting with 4-fluoro-2-methylphenyl isothiocyanate and using the process of Gonda J. and Kristian P. (*Collect Czech Chem Commun* 1990, 55, 752–60), 4-fluoro-2-bromomethylphenyl isothiocyanate (m.p. <40°) is prepared in a yield of 56%. This derivative, condensed under the same conditions as those described in Example 1, allows 650 mg (yield: 76%) of expected base (m.p.=113°) to be prepared, which product is salified to give 770 mg (yield: 72%) of white crystals of formula 8:

(8)

Empirical formula: $C_{28}H_{33}F_2N_3O_5S$; Molecular mass: 561.63; Melting point: 148–149°; IR (KBr): υ (N=C): 1614; ($COO^{31-}$): 1570 cm$^{-1}$. NMR (CDCl$_3$) δ: 1.7–2.15 (m, 6H); 2.34 (q.d., 2H); 2.3–3.4 (m, 4H); 3.07 (s, 3H); 3.5–3.8 (m, 2H); 3.86 (s, 2H); 3.91 (t, 2H); 4.8–5.2 (m, 1H); 6.26 (s, 2H); 6.45–6.8 (m, 2H); 6.9–7.15 (m, 4H); 7.15–7.3 (m, 1H); 10.5–14 (m, 2H).

EXAMPLE 9

6-Chloro-N-methyl-N-[1-[3-(4-fluorophenoxy)propyl]-piperid-4-yl]-4H-3,1-benzothiazin-2-amine hydrogen maleate (9).

According to the process detailed in Example 8, 4-chloro-2-bromomethylphenyl isothiocyanate (m.p.=65°) is prepared in a yield of 70%, which product is condensed according to the procedure described in Example 1 to give 710 mg of expected base (m.p.=125°) which is salified with maleic acid to give 820 mg (yield: 81%) of off-white crystals of formula 9:

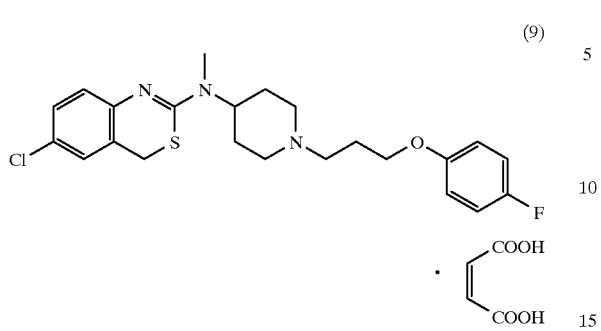

Empirical formula: $C_{27}H_{31}ClFN_3O_5S$; Molecular mass: 564.06; Melting point: 155–156°; IR (KBr): υ (N=C): 1607; ($COO^{31}$): 1558 $cm^{-1}$. NMR (DMSO $d_6$) δ: 1.7–2.3 (m, 6H); 3.01 (s, 3H); 2.9–3.5 (m, 4H); 3.5–3.75 (m, 2H); 3.96 (s, 2H); 4.01 (t, 2H); 4.45–4.8 (m, 1H); 6.01 (s, 2H); 6.8–7 (m, 3H); 7.05–7.4 (m, 4H); 8.5–11 (m, 2H).

EXAMPLE 10

6-Methoxy-N-methyl-N-[1-[3-(4-fluorophenoxy)propyl]-piperid-4-yl]-4H-3,1-benzothiazin-2-amine dihydrogen maleate (10).

By condensing 568 mg (2.10 mmol) of 4-methoxy-2-bromomethylphenyl isothiocyanate, prepared according to Example 8, and by condensing it with N-methyl-1-[3-(4-fluorophenoxy)propyl]-4-piperidinamine dihydrochloride (748 mg) according to the process described in Example 1, but doubling the amount of maleic acid, 615 mg (yield: 41%) of white crystals of formula 10 are prepared:

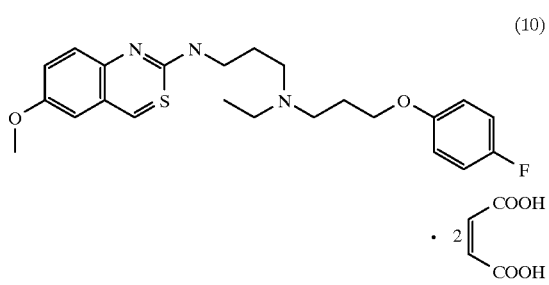

Empirical formula: $C_{32}H_{38}FN_3O_{10}S$; Molecular mass: 675.708; Melting point: 136–137°; IR (KBr): υ (N=C): 1607; ($COO^{31}$): 1577 $cm^{-1}$. NMR ($CDCl_3$) δ: 1.7–2.3 (m, 6H); 3 (s, 3H); 2.9 –3.4 (m, 4H); 3.5–3.8 (m, 2H); 3.71 (s, 3H); 3.96 (s, 2H); 4.04 (s, 2H); 4.45–4.75 (m, 1H); 6.14 (s, 4H); 6.75–6.85 (m, 2H); 6.85–7.05 (m, 3H); 7.1–7.3 (m, 2H); 8.5–12.5 (m, 4H).

EXAMPLE 11

N-Methyl-N-[1-[4-(3,4-difluorophenoxy)butyl]piperid-4-yl]-4H-3,1-benzothiazin-2-armine hydrogen maleate (11).

Starting with 654 mg (2.19 mmol) of N-methyl-1-[4-(3, 4-difluorophenoxy)butyl]-4-piperidinamine base prepared according to A. M. Ismaiel et al., *J Med Chem* (1993) 36 pp. 2519–2525 and by condensing them with 500 mg (2.19 mmol) of ortho-bromomethylphenyl isothiocyanate according to the process described in Example 1, white crystals of formula 11 are prepared in a yield of 66%:

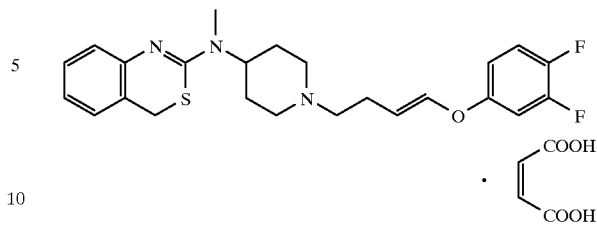

Empirical formula: $C_{28}H_{33}F_2N_3O_5S$; Molecular mass: 561.626; Melting point: 130–131°; IR (KBr): υ (C=N): 1606; ($COO^{31}$): 1564 $cm^{-1}$. NMR (DMSO $d_6$) δ: 1.5–2.3 (m, 8H); 3.03 (s, 3H); 2.8–3.35 (m, 4H); 3.4–4.2 (m, 2H); 3.97 (s, 2H); 4.01 (t, 2H); 4.55–4.85 (m, 1H); 6.05 (s, 2H); 6.7–7.5 (m, 7H); 8.3–11.2 (m, 2H).

EXAMPLE 12

N-[1-[4-(3,4-Difluorophenoxy)butyl]piperid-4-yl]-4H-3,1-benzothiazin-2-amine hydrogen maleate (12).

1.1 g (3.07 mmol) of 1-[4-(3,4-difluorophenoxy)butyl]-4-piperidinamine dihydrochloride (m.p.=240–3°) is condensed with 700 mg (3.07 mmol) of ortho-bromomethylphenyl isothiocyanate according to Example 1 and gives 1.01 g of expected base (m.p.=131°) which is salified with maleic acid to give 1.16 g (yield: 69%) of white crystals of formula 12:

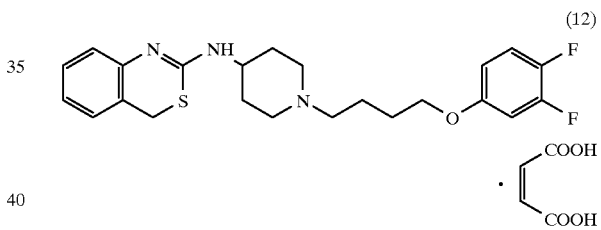

Empirical formula: $C_{27}H_{31}F_2N_3O_5S$; Molecular mass: 547.606; Melting point: 103–104°; IR (KBr): υ (N—H): 3260; (C=N); 1606; ($COO^{31}$): 1562 $cm^{-1}$. NMR (DMSO $d_6$) δ: 1.4–2.1 (m, 6H); 2.1–2.5 (m, 2H); 2.5–3.1 (m, 4H); 3.1–3.6 (m, 2H); 3.7–4.5 (m, 5H); 6.22 (s, 2H); 6.4–6.9 (m, 2H); 6.9–7.7 (m, 5H); 10–12.5 (m, 2H).

EXAMPLE 13

N-[1-[4-(4-Chlorophenoxy)butyl]piperid-4-yl]-4H-3,1-benzothiazin-2-amine hydrogen maleate (13).

780 mg (2.19 mmol) of 1-[4-(4-chlorophenoxy)butyl]-4-piperidinamine dihydrochloride (m.p.=224–6°) are treated with 500 mg (2.19 mmol) of ortho-bromomethylphenyl isothiocyanate according to the process described in Example 1, to give 860 mg (yield: 71%) of white powder of formula 13:

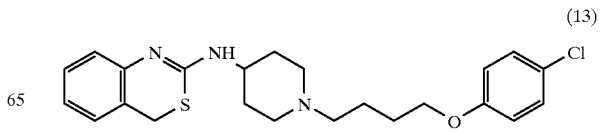

-continued

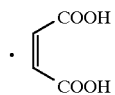

Empirical formula: $C_{27}H_{32}ClN_3O_5$ S; Molecular mass: 546.067; Melting point: 158–159°; IR (KBr): υ (N—H): 3230; (N=C): 1607 cm$^{-1}$. NMR (DMSO d$_6$) δ: 1.5–1.9 (m, 6H); 1.9–2.4 (m, 2H); 2.8–3.7 (m, 6H); 3.91 (s, 2H); 3.98 (t, 2H); 3.8–4.4 (m, 1H); 6.01 (s, 2H); 6.8–7.05 (m, 4H); 7.05–7.2 (m, 2H); 7.2–7.65 (m, 3H); 8.5–10.5 (m, 2H).

EXAMPLE 14

N-[1-[2-hydroxy-3-(4-fluorophenoxy)propyl]piperid-4-yl]-4H-3,1-benzothiazin-2-amine dihydrochloride hemihydrate (14).

14-1: 1-Benzyl-4-tert-butoxycarbonylaminopiperidine: a mixture of 40.8 ml (38 g, 0.2 mol) of 1-benzyl-4-piperidinamine in 220 ml of 1 N sodium hydroxide and 110 ml of tert-butanol in a 1 l reactor is cooled on a bath of cold water and then treated dropwise with a solution of 43.7 g (0.2 mol) of di-tert-butyl dicarbonate in 40 ml of tert-butanol, while maintaining the temperature at about 25°. Stirring is continued for 5 h at 25° and the mixture is then extracted several times with methylene chloride, washed with water, dried over sodium sulfate, filtered and then evaporated to dryness. The residue is taken up in 250 ml of isopropyl ether, stirred, filtered and drained to give 58.8 g (yield: 84%) of white powder of formula 14-1:

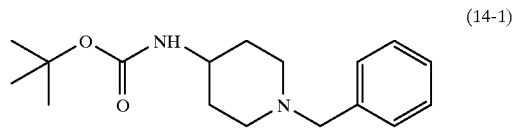

(14-1)

Empirical formula: $C_{17}H_{26}N_2O_2$; Molecular mass: 190.29; Melting point: 121–122°

14-2: 4-tert-Butoxycarbonylaminopiperidine hydrochloride: a solution of 48 g (0.165 mol) of the above compound in 480 ml of methylene chloride in a 1 l reactor is cooled to 0° and then treated dropwise with 26 g (0.182 mol) of α-chloroethoxycarbonyl chloride and the mixture is allowed to return slowly to 25° and is stirred overnight at this temperature. The mixture is evaporated to dryness to give a pink oil which eventually crystallizes. The residue is diluted with 480 ml of methanol and refluxed for 2 h, and the mixture is then evaporated to dryness to give a beige-colored solid which is taken up in ether and stirred for 1 h. The insoluble material is filtered off, drained and dried to give 39.1 g of white powder (yield: 97%) of formula 14-2:

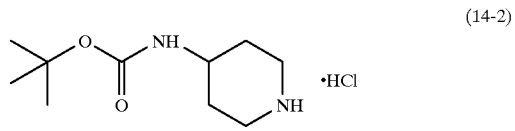

(14-2)

Empirical formula: $C_{10}H_{21}ClN_2O_2$; Molecular mass: 236.72; Melting point: 151–152°; IR (KBr) υ (N—H): 3296; (C=O): 1716 cm$^{-1}$.

14-3: 4-tert-Butoxycarbonylamino-1-[2-hydroxy-3-(4-fluorophenoxy)propyl]piperidine: a solution of 10 g (49.8 mmol) of base of the main compound above in 100 ml of dry methanol in a 250 ml round-bottomed flask is treated with 10 g (59.62 mmol) of 1-(4-fluorophenoxy)-2,3-epoxypropane (prepared according to W. S. Di Menna et al., *J Med Chem* (1978), 21, pp. 1073–1076, b.p. 94°/0.25 mbar, yield: 72%) and then stirred at 25° overnight. The mixture is evaporated to dryness, triturated from isopropyl ether, filtered and drained to give off-white crystals (m=15.1 g; yield: 80%) of formula 14-3:

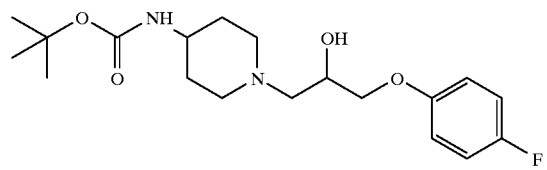

(14-3)

Empirical formula: $C_{19}H_{29}FN_2O_4$; Molecular mass: 368.44; Melting point: 129–130°; IR (KRr) [sic] υ (N—H): 3420; (O—H): 3400–3200; (C=O): 1709 cm$^{-1}$.

14-4: 1-[2-Hydroxy-3-(4-fluorophenoxy)propyl]-4-piperidinamine dihydrochloride: a mixture of 11 g (30 mmol) of the above compound in 20 ml of ethanol and 33 ml of a 3 N solution of hydrochloric acid in ethanol in a 250 ml round-bottomed flask is stirred over the weekend at 25°. The insoluble material is filtered off, rinsed with ether and dried to give 8.1 g (yield: 79%) of white powder of formula 14-4:

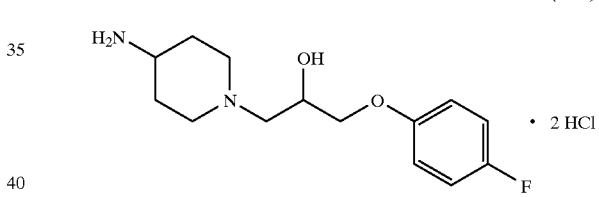

(14-4)

Empirical formula: $C_{14}H_{23}Cl_2FN_2O_2$; Molecular mass: 341.25; Melting point: 222–223°; IR (KBr) υ (OH, NH): 3360; (C—O—C): 1203 cm$^{-1}$.

14-5: N-[1-[2-Hydroxy-3-(4-fluorophenoxy)propyl]piperid-4-yl]-4H-3,1-benzothaizin-2-amine dihydrochloride hemihydrate (14): a solution of 500 mg (2.19 nmol) of ortho-bromomethylphenyl isothiocyanate in 7 ml of toluene is treated with 748 mg (2.19 mmol) of the above compound in the presence of 1.22 ml (8.■ mmol) of triethylamine. The mixture is then maintained at 80° for 5 h 30. After cooling to 25° the mixture is filtered, the insoluble material is rinsed with toluene and the filtrate is evaporated to dryness to give a residue which is taken up in methylene chloride. The organic phase is washed with water and with brine, dried over sodium sulfate and evaporated to dryness. The crude residual oil is purified by flash chromatography, eluting with a 95 CH$_2$Cl$_2$/4.5 MeOH/0.5 NH$_4$OH mixture to give, after evaporation, 720 mg (79%) of a pale yellow oil which crystallizes (m.p.=117–118°).

This residue is converted to the hydrochloride in the usual manner with an EtOH/HCl solution. After recrystallization from ethanol, 600 mg (yield: 63%) of white crystals of formula 14 are obtained:

(14)

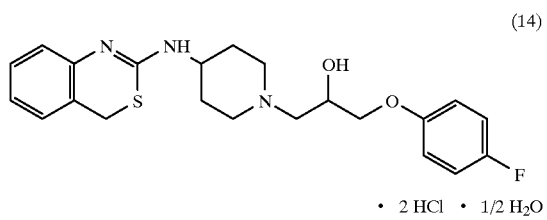

· 2 HCl · 1/2 H₂O

Empirical formula: $C_{22}H_{26}N_3FO_2S$, 2HCl, ½H₂O; Molecular mass: 497.45; Melting point: 239–240°; (Melting point of the base: 117–118°); IR (base) (KBr) υ (N—H): 3422; (O—H): 3600–3300; (N═C): 1608 cm⁻¹. NMR (base) (DMSO d₆): 1.3–1.7 (m, 2H); 1.75–2 (m, 2H); 2–2.25 (m, 2H); 2.25–2.6 (m, 2H); 2.88 (t, 2H); 3.9 (s, 2H); 3.7–4.2 (m, 4H); 4.85 (a, 1H); 6.5–7.6 (m, 9H).

EXAMPLE 15

N-Methyl-N-[1-[2-hydroxy-3-(4-fluorophenoxy)propyl]-piperid-4-yl]-4H-3,1-benzothiazin-2 -amine dihydrochloride (15).

15-1: N-Methyl-1-benzyl-4-piperidinamine: to a mixture of 37.85 g (0.2 mol) of 1-benzyl-4-piperidone in 150 ml of petroleum ether and 40 ml of acetic acid are added 13.51 g (0.2 mol) of methylamine hydrochloride and the mixture is stirred for 3 h at 25°. 90 ml of methanol are then added, followed by dropwise addition of 24 ml (18.6 g or 0.2 mol) of 8 M borane pyridine and stirring is continued for a further 5 h at 25°. The mixture is hydrolyzed by dropwise addition of 100 ml of 6 N hydrochloric acid with vigorous stirring. The base is then liberated by addition of caustic soda to pH 12, extracted with ether and then washed with brine, dried over sodium sulfate and evaporated to dryness to give a greenish oil (m=38 g) . Purification on 1000 g of silica by flash chromatography gives, after elution with a 95 CH₂Cl₂/4.5 MeOH/0.5 NH₄OH mixture and evaporation to dryness, a colorless oil (m =32.5 g; yield: 79%) of formula 15-1:

(15-1)

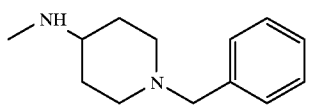

Empirical formula: $C_{13}H_{20}N_2$; Molecular mass: 204.31; Colorless oil 15-2: N-tert-Butoxycarbonyl-N-methyl-1-benzyl-4-piperidinamine: a solution of 18.4 g (90 mmol) of the above compound in 120 ml of tert-butanol is treated with 100 ml of aqueous normal sodium hydroxide and then dropwise with 19.65 g (90 mmol) of di-tert-butyl dicarbonate and stirring is continued overnight at 25°. The mixture is extracted three times with ether and the organic phase is then washed with water and with brine, dried over sodium sulfate and evaporated to dryness to give an amber-colored oil (m =25.8 g; yield: 84%) of formula 15-2, which is used without further purification in the following step:

(15-2)

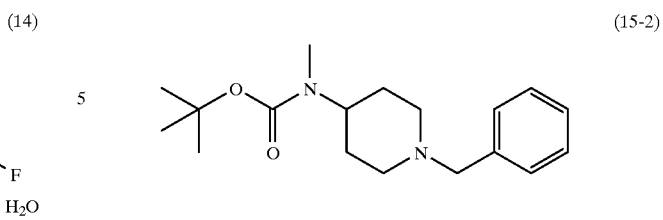

Empirical formula: $C_{18}H_{28}N_2O_2$; Molecular mass: 304.42; Amber-colored oil; NMR (CDCl₃) δ: 1.43 (s, 9H); 1.5–1.9 (m, 4H); 2 (t.d, 2H); 2.7 (s, 3H); 2.8–3 (m, 2H); 3.46 (s, 2H); 3.6–4.2 (m, 1H); 7.15–7.35 (m, 5H).

15-3: N-Methyl-N-tert-butoxycarbonyl-4-piperidinamine hydrochloride: a solution of 24.35 g (80 mmol) of the above derivative in 200 ml of methylene chloride is cooled to 0° and then treated dropwise with 9.50 ml (12.5 g or 88 mmol) of a-chloroethyl chloroformate, after which it is allowed to warm to 25° and stirring is continued for a further 18 hours. The mixture is evaporated to dryness and the residue is taken up in 200 ml of methanol and refluxed for 2 h. After evaporation to dryness under vacuum, the residue is triturated from ether and the insoluble material is filtered off, rinsed, drained and dried to give a white powder (m=19.6 g; yield: 98%) of formula 15-3:

(15-3)

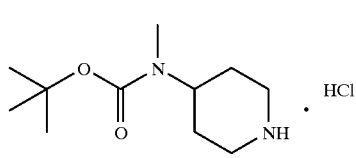

Empirical formula: $C_{11}H_{23}ClN_2O_2$; Molecular mass: 250.76; Melting point:>250°;

15–4: 1-[2-Hydroxy-3-(4-fluorophenoxy)propyl]-N-methyl-4-piperidinamine dihydrochloride: a solution of 3 g (14 mmol) of the above base in 30 ml of dry methanol is treated with 2.35 g (14 mmol) of 1-(4-fluorophenoxy)-2,3-epoxypropane and the mixture is stirred for 24 h at 25° and then evaporated to dryness in order to obtain the compound of formula 15-4-1 which is hydrolyzed directly in 30 ml of 3 N hydrochloric acid, maintaining the mixture at reflux for 2 h 30.

(15-4-1)

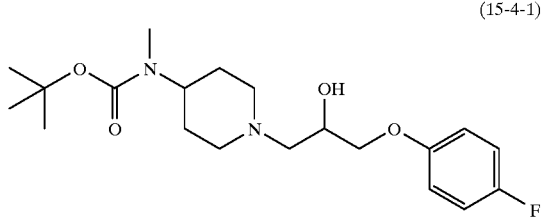

The mixture is evaporated to dryness and taken up in 20 ml of ethanol. The dihydrochloride of formula 15-4 precipitates on addition of ether and is recovered in the usual manner (m=4.20 g; yield: 84%).

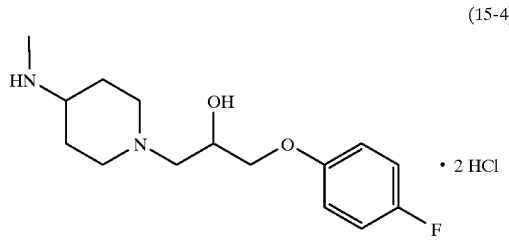

Empirical formula: $C_{15}H_{25}Cl_2FN_2O_2$; Molecular mass: 355.28; Melting point: 198–200°; NMR (DMSO d$_6$) δ: 1.8–2.45 (m, 4H); 2.8–4.2 (m, 10H); 3.37 (s, 3H); 4.25–4.6 (m, 1H); 5.85–6.2 (m, 1H); 6.8–7.4 (m, 4H); 9.3–9.8 (m, 2H).

15-5: N-Methyl-N-[1-[2-hydroxy-3-(4-fluorophenoxy)-propyl]piperid-4-yl]-4H-3,1-benzothiazin-2-amine dihydrochloride: working as described in Example 14-5 but starting with 860 mg (2.41 mmol) of the above derivative and 550 mg (2.41 mmol) of ortho-bromomethylphenyl isothiocyanate, 820 mg (yield: 68%) of white crystals of formula 15 are prepared:

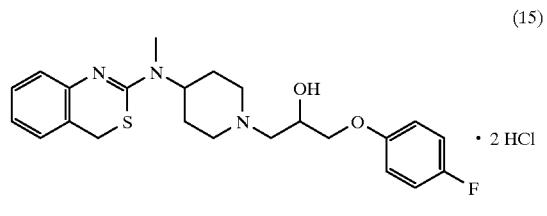

Empirical formula: $C_{23}H_{30}Cl_2FN_3O_2S$; Molecular mass: 502.46; Melting point: 249–251°; IR (KBr) υ (OH): 3238; (NH$^+$): 2473; (N=C): 1622 cm$^{-1}$. NMR (DMSO d$_6$) δ: 1.7–2.2 (m, 2H); 2.25–2.8 (m, 2H); 2.9–3.5 (m, 5H); 3.27 (s, 3H); 3.55–3.85 (m, 2H); 3.94 (d, 2H); 4.29 (s, 2H); 4.28–4.5 (m, 1H); 4.6–6.3 (m, 2H); 6.8–8 (m, 8H), 10.3–10.5 (m, 1H).

EXAMPLE 16

N-Methyl-N-[1-(4-phenoxybutyl)piperid-4-yl]-4H-3,1-benzo-thiazin-2-amine hydrogen maleate (16).

16-1: N-Methyl-N-[1-benzylpiperid-4-yl]-4H-3,1-benzothiazin-2-ylamine: a mixture of 6.32 g (22.8 mmol) of N-methyl-1-benzyl-4-piperidinamine dihydrochloride (prepared as described in Example 15-1) and 5.2 g (22.8 mmol) of 2-bromomethylphenyl isothiocyanate and 12.7 ml of triethylamine (91.2 mmol) in 60 ml of toluene is maintained at 80° for 1 h with magnetic stirring. After cooling to 40° the mixture is evaporated to dryness under vacuum and then taken up in water and extracted several times with methylene chloride, after which it is washed with water and with brine and dried over sodium sulfate. After removal of the inorganic salt, the mixture is evaporated to dryness under vacuum and then purified by flash chromatography on 450 ml of silica, eluting with a 97.5 CH$_2$Cl$_2$/2.5 MeOH mixture. The fractions containing the expected compound are combined and evaporated to dryness to give 7.2 g (yield: 86%) of a pale yellow oil of formula 16-1:

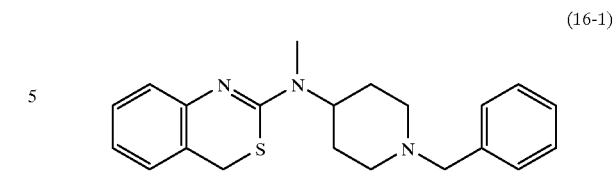

Empirical formula: $C_{21}H_{25}N_3S$; Molecular mass: 351.49; NMR (CDCl$_3$) δ: 1.6–1.75 (m, 2H); 1.89 (q.d, 2H); 2.13 (t.d, 2H); 2.9–3.05 (m, 2H); 3.11 (s, 3H); 3.54 (s, 2H); 3.85 (s, 2H); 4.3–4.55 (m, 1H); 6.85–7.15 (m, 3H); 7.15–7.45 (m, 6H).

16-2: N-Methyl-N-(piperid-4-yl)-4H-3,1-benzothiazin-2-amine hydrochloride: a solution of 400 mg (1.14 mmol) of the above base in 4 ml of 1,2-dichloroethane is cooled on a bath of ice and then treated dropwise with 0.135 ml (1.25 mmol) of α-chloroethyl chloroformate, after which it is allowed to warm slowly to 25° and is stirred for a further 3 h at this temperature. The mixture is evaporated to dryness under vacuum, taken up in 4 ml of methanol and refluxed for 1 h. The mixture is evaporated to dryness to give an oil which crystallizes. The product is taken up in ether and the white crystals (m=310 mg; yield: 91%) of formula 16-2 are filtered off:

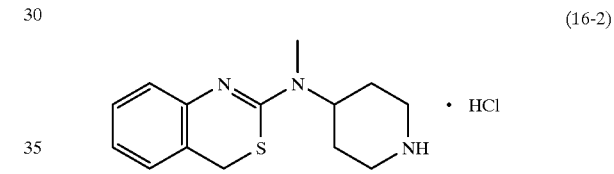

Empirical formula: $C_{14}H_{20}ClN_3S$; Molecular mass: 297.84; Melting point: 200° NMR (DMSO d$_6$) δ: 1.6–1.95 (m, 2H); 2–2.35 (m, 2H); 2.7–3.3 (m, 4H); 3.34 (d, 3H); 4.04 (s, 2H); 4.4–4.9 (m, 1H); 6.8–7.5 (m, 4H); 9.1 (s, 2H).

16-3: N-Methyl-N-[1-(4-phenoxybutyl)piperid-4-yl]-4H-3,1-benzothiazin-2-amine hydrogen maleate: a suspension of 284 mg (0.95 mmol) of the above compound in 3 ml of dry DMF is treated successively with 182 mg (0.8 mmol) of 1-bromo-4-phenoxybutane and 210 mg (2 mmol) of Na$_2$CO$_3$ and then heated at 80° for 2 h 30. After cooling to 25° the mixture is extracted several times with ethyl acetate, washed with water and with brine and dried over sodium sulfate. After removal of the inorganic salt, the mixture is evaporated to dryness to give an oil which is purified by flash chromatography, eluting with a 97.5 CH$_2$Cl$_2$/2.25 MeOH/ 0.25 NH$_4$OH mixture. The fractions containing the expected derivative are combined and evaporated to dryness and the base obtained is salified with maleic acid in the usual manner: white crystals (m=290 mg; yield: 58%) of formula 16:

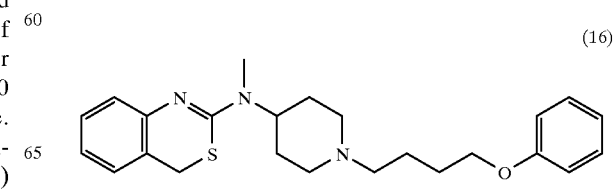

-continued

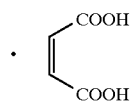

Empirical formula: $C_{28}HN_{35}N_3O_5S$; Molecular mass: 525.65; Melting point: 119–121°; IR (KBr) υ (COO$^{31}$): 1566 cm$^{-1}$. NMR (CDCl$_3$) δ: 1.75–2.2 (m, 6H); 2.25–2.6 (m, 2H); 2.85–3.2 (m, 4H); 3.14 (s, 3H); 3.6–3.8 (m, 2H); 3.92 (s, 2H); 4.01 (t, 2H); 4.95–5.25 (m, 1H); 6.3 (s, 2H); 6.8–7.2 (m, 6H); 7.2–7.4 (m, 3H); 11.5–13.5 (m, 2H).

EXAMPLE 17

N-[1-[4-(4-Fluorophenoxy)butyl]piperid-4-yl]-4H-3,1-benzothiazin-2-amine (4).

17-1: 1-[4-[4-Fluorophenoxy)butyl]piperid-4-yl isothiocyanate: a solution of 470 mg (2 mmol) of dipyridyl thiocarbonate in 5.5 ml of dry methylene chloride is treated dropwise at 25° under a nitrogen atmosphere with a solution of 515 mg of 1-[4-(4-fluorophenoxy)butyl]-4-piperidinamine (1.95 mmol) in 3 ml of methylene chloride. After stirring for 20 minutes, the solution is diluted with 30 ml of methylene chloride, washed with water and with brine and then dried over sodium sulfate. By evaporation, a slightly orange-colored oil (m=600 mg; yield: 97%) of formula 17-1 is recovered.

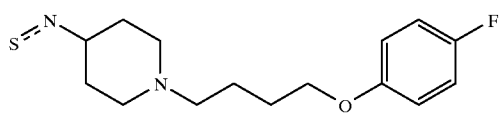
(17-1)

Empirical formula: $C_{16}H_{21}FN_2OS$; Molecular mass: 308.408; IR (NaCl slides) υ (N=C=S): 2105 cm$^{-1}$. NMR (CDCl$_3$) δ: 1.5–2.2 (m, 8H); 2.2–2.5 (m, 4H); 2.5–2.85 (m, 2H); 3.6–3.85 (m, 1H); 3.90 (t, 2H); 6.73–6.85 (m, 2H); 6.85–7.05 (m, 4H).

17-2: 1-[1-[4-(4-Fluorophenoxy)butyl]piperid-4-yl]-3-(2-hydroxymethylphenyl)thiourea: to a solution of 800 mg (3 mmol) of the above isothiocyanate in 8 ml of dry dioxane heated to 60° is added dropwise a solution of 370 mg (3 mmol) of 2-aminobenzyl alcohol in 4 ml of dioxane, followed by heating for a further 2 hours at this temperature. The mixture is allowed to cool to 25° and the white crystals (m=980 mg; yield: 76%) of thiourea of formula 17-2 are then filtered off.

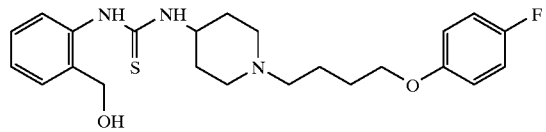
(17-2)

Empirical formula: $C_{23}H_{30}FN_3O_2S$; Molecular mass: 431.55; Melting point: 116–117°; NMR (CDCl$_3$) δ: 1.25–1.9 (m, 6H); 1.95–2.25 (m, 4H); 2.36 (t, 2H); 2.7–2.95 (m, 2H); 2.95–3.5 (m, 1H); 3.90 (t, 2H); 4–4.4 (m, 1H); 4.63 (s, 2H); 6.12 (d, 1H); 6.7–6.85 (m, 2H); 6.85–7.05 (m, 2H); 7.15–7.5 (m, 4H); 8.31 (s, 1H).

17-3: N-[1-[4-(4-Fluorophenoxy)butyl]piperid-4-yl]-4H-3,1-benzothiazin-2-amine (4'): a solution of 610 mg (1.4 mmol) of the above thiourea in 5 ml of concentrated HCl is refluxed for 10 minutes. After cooling to 25°, crushed ice is added and the mixture is basified to pH 12 using concentrated sodium hydroxide solution. The organic base liberated is extracted with ethyl acetate and dried over sodium sulfate and then evaporated to dryness. The solid residue is then recrystallized from boiling alcohol to give white crystals (m=470 mg; yield: 81%) of formula 4', melting at 133°, the spectral characteristics of which are identical to those of the base of the derivative prepared in Example 4:

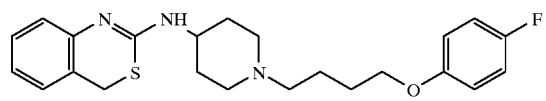
(4')

EXAMPLE 18

6,7-Dimethoxy-N-[1-[3-(3,4-difluorophenoxy)propyl]-piperid-4-yl]-4H-3,1-benzothiazin-2-amine dihydrogen maleate (18).

18-1: 2-Amino-4,5-dimethoxybenzyl alcohol: to a suspension of 1.90 g (50 mmol) of LiAlH$_4$ in 150 ml of dry THF cooled to 0° are added dropwise over 1 hour 10.50 g (50 mmol) of methyl 2-amino-4,5-dimethoxybenzoate dissolved in 150 ml of THF. The mixture is stirred for 1 h at this temperature and is then allowed to warm to 25° and is stirred for a further one hour at 25°. The mixture is cooled to 0° and treated dropwise with 30 ml of ethyl acetate. The insoluble material is filtered off on a silica filter and rinsed with the same solvent, and the filtrate is evaporated to dryness. The residue is taken up in methylene chloride and rinsed with a small amount of saturated brine, dried and evaporated and then purified by flash chromatography. The residue is triturated from a small amount of isopropyl ether to give pink crystals of formula 18-1 which eventually darken (m=6.5 g; yield: 65%).

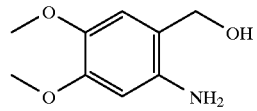
(18-1)

Empirical formula: $C_9H_{13}NO_3$; Molecular mass: 183.30; Melting point: 76–77°; NMR (CDCl$_3$) δ: 3.1 (s, 3H); 3.80 (s, 3H); 3.87 (s, 3H); 4.6 (s, 2H); 6.3 (s, 1H); 6.65 (s, 1H).

18-2: 1-[3-(3,4-Difluorophenoxy)propyl]piperid-4-yl isothiocyanate: working as described in Example 17-1 but starting with 22.3 mmol of 1-[3-(3,4-difluorophenoxy)-propyl]-4-piperidinamine and condensing them with 6.14 g (23 mmol) of dipyridyl thiocarbonate, the isothiocyanate of formula 18-2 is prepared in a yield of 62%:

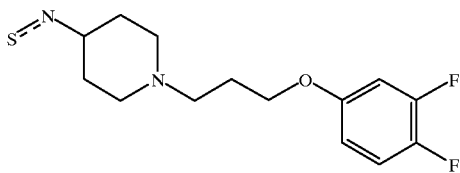

Empirical formula: $C_{17}H_{22}F_2N_2OS$; Molecular mass: 313.38; Amber-colored oil. IR (NaCl slides): υ (N=C=S): 2106 cm$^{-1}$ NMR (CDCl$_3$) δ: 1.18–2.1 (m, 6H); 2.2–2.45 (m, 2H); 2.49 (t, 2H); 2.5–2.75 (m, 2H); 3.65–3.85 (m, 1H); 3.93 (t, 2H); 6.5–6.8 (m, 2H); 7.03 (q, 1H).

18-3: 1-[1-[3-(3,4-Difluorophenoxy)propyl]piperid-4-yl]-3-(2-hydroxymethyl-4,5-dimethoxyphenyl)thiourea: using the process described in Example 17-2 but starting with 760 mg (4.15 mmol) of the derivative 18-1 and by condensing it with 1.40 g (5.6 mmol) of the above compound, 1.62 g (yield: 79%) of white crystals of formula 18-3 are prepared:

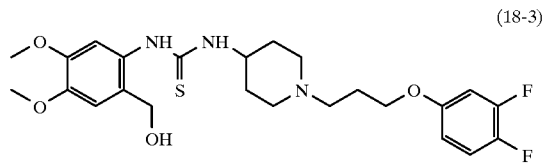

Empirical formula: $C_{24}H_{31}F_2N_3O_4S$; Molecular mass: 495.57; Melting point: 168°; NMR (DMSO d$_6$): δ: 1.3–1.6 (m, 2H); 1.75–2.1 (m, 6H); 2.39 (t, 2H); 2.7–2.9 (m, 2H); 3.72 (s, 3H); 3.77 (s, 3H); 3.98 (t, 2H); 3.9–4.2 (m, 1H); 4.36 (d, 2H); 5.09 (t, 1H); 6.7–6.83 (m, 1H); 6.85 (s, 1H); 7 (s, 1H); 7–7.2 (m, 1H); 7.2–7.5 (m, 2H); 8.84 (s, 1H).

18-4: 6,7-Dimethoxy-N-[1-[3-(3,4-difluorophenoxy)propyl]-piperid-4-yl]-4H-3,1-benzothiazin-2-amine dihydrogen maleate (18): working according to the procedure of Example 17-3, the derivative of formula 18 is prepared in a yield of 76%, starting with 2.86 mmol of compound 18-3:

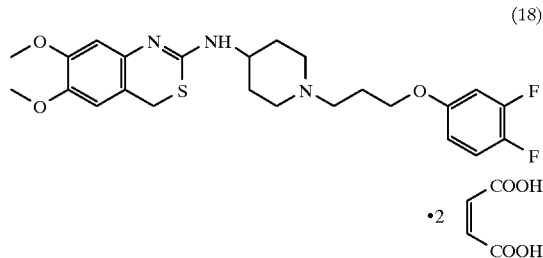

Empirical formula: $C_{32}H_{37}F_2N_3O_{11}S$; Molecular mass: 709.69; Melting point: 180–182°; NMR (DMSO d$_6$) δ: 1.5–1.9 (m, 2H); 1.9–2.4 (m, 4H); 2.9–3.4 (m, 4H); 3.4–3.7 (m, 2H); 3.72 (s, 6H); 3.9 (s, 2H); 4.05 (t, 2H); 3.9–4.4 (m, 1H); 6.13 (s, 4H); 6.53 (s, 1H); 6.7–6.85 (m, 1H); 6.79 (s, 1H); 7–7.2 (m, 1H); 7.38 (q, 1H); 7.3–7.7 (m, 1H); 8.6–9.8 (m, 4H).

EXAMPLE 19

6,7-Dimethoxy-N-methyl-N-[1-[3-(3,4-difluorophenoxy)-propyl]piperid-4-yl]-4H-3,1-benzothiazin-2-amine dihydrogen maleate (19).

A solution of 890 mg (1.86 mmol) of crude 6,7-dimethoxy-N-[1-[3-(3,4-difluorophenoxy)propyl]piperid-4-yl]-4H-3,1-benzothiazin-2-amine base prepared in Example 18 in 9 ml of dry DMF is treated at 0° with 100 mg (2.5 mmol) of 60% NaH and is stirred for 30 minutes, after which 290 mg (0.22 ml or 2.05 mmol) of MeI are added and the mixture is allowed to warm slowly to 25°. After stirring for 1 h 15 at this temperature, the DMF is removed under vacuum and the residue is taken up in methylene chloride, washed with water and with brine and then dried over sodium sulfate. After concentration to dryness, the residual oil is purified by flash chromatography on a column of silica, eluting with a 95 CH$_2$Cl$_2$/4.5 MeOH/0.5 NH$_4$OH mixture. 560 mg of oil are obtained (yield: 62%), which product is salified with maleic acid in the usual manner to give 710 mg (yield: 52%) of white crystals of formula 19:

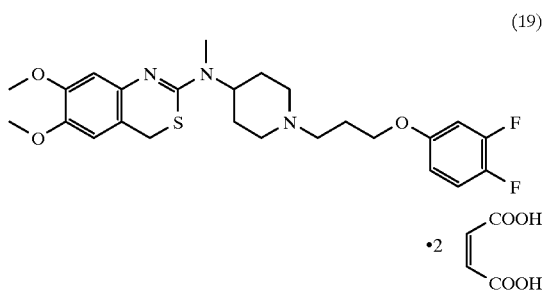

Empirical formula: $C_{33}H_{39}F_2N_3O_{11}S$; Molecular mass: 723.72; Melting point: 134°; NMR (DMSO d$_6$) δ: 1.75–2.3 (m, 6H); 3.03 (s, 3H); 3.1–3.4 (m, 4H); 3.55–3.78 (m, 2H); 3.73 (s, 3H); 3.74 (s, 3H); 3.94 (s, 2H); 4.08 (t, 2H); 4.45–4.85 (m, 1H); 6.16 (s, 4H); 6.57 (s, 1H); 6.81 (s, 1H); 6.75–6.85 (m, 1H); 7.05–7.2 (m, 1H); 7.41 (q, 1H); 8.2–10.5 (m, 4H).

EXAMPLE 20

6-Methyl-N-[1-[3-(3,4-difluorophenoxy)propyl]piperid-4-yl-3,1-benzothiazin-2-armine hemifumarate (20).

20-1: 2-Amino-5-methylbenzyl alcohol: this compound of formula 20-1 is prepared in a yield of 68% by adapting the procedure of Example 18-1:

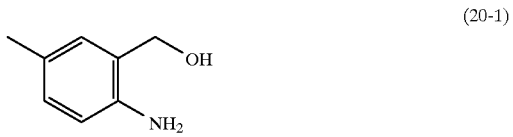

Empirical formula: $C_8H_{11}NO$; Molecular mass: 137.18; Melting point: 124–125°; NMR (DMSO d$_6$) δ: 2.13 (s, 3H); 4.33 (d, 2H); 4.68 (s, 2H); 4.95 (t, 1H); 6.51 (d, 1H); 6.77 (dd, 1H); 6.86 (s, 1H).

20-2: 1-[1-[3-(3,4-Difluorophenoxy)propyl]piperid-4-yl]-3-(2-hydroxymethyl-4-methylphenyl)thiourea: condensation of 410 mg (3 mmol) of the above compound with 1.05 g (3.3 mmol) of 1-[3-(3,4-difluorophenoxy)propyl]piperid-4-yl isothiocyanate (18-2) according to Example 18-3 gives 1.18 g (87% yield) of a gummy residue of formula 20-2 which is used without further purification in the following step:

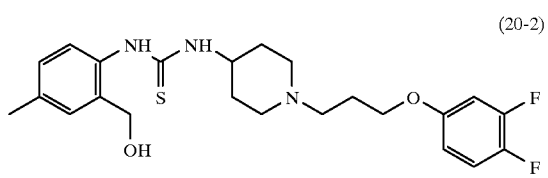

(20-2)

20-3: 6-Methyl-N-[1-[3-(3,4-difluorophenoxy)propyl]-piperid-4-yl]-4H-3, 1-benzothiazin-2-amine hemifumarate: cyclization of 1.08 g (2.4 mmol) of the above crude base according to the process described in Example 18-4 gives a 63% yield of white crystals of formula 20:

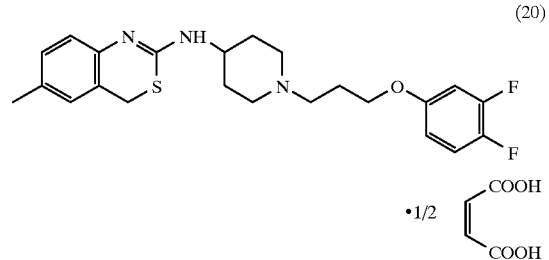

(20)

Empirical formula: $C_{25}H_{29}F_2N_3O_3S$; Molecular mass: 489.57; Melting point: 183°; NMR (DMSO $d_6$) δ: 1.4–1.75 (m, 2H); 1.75–2.05 (m, 4H); 2.05–2.45 (m, 2H); 2.24 (m, 3H); 2.4–2.75 (m, 2H); 2.8–3.2 (m, 2H); 3.86 (s, 2H); 3.8–4.2 (m, 3H); 6.56 (s, 1H); 6.65–7.5 (m, 7H); 8.5–10 (m, 1H).

EXAMPLE 21

N-Methyl-N-[1-[4-(4-methylphenoxy)butyl]piperid-4-yl]-4H-3,1-benzothiazin-2-amine hydrogen maleate (21).

Condensation of 700 mg (2.35 mmol) of N-methyl-N-[4-piperidyl]-4H-3,1-benzothiazin-2-amine, obtained in Example 16-2, with 467 mg (2.35 mmol) of 1-(4-methylphenoxy)-4-chlorobutane in 8 ml of dry DMF in the presence of 630 mg (5.86 mmol) of 98 $K_2CO_3$/02 KI according to the process described in Example 16-3 gives a 49% yield of white crystals of formula 21:

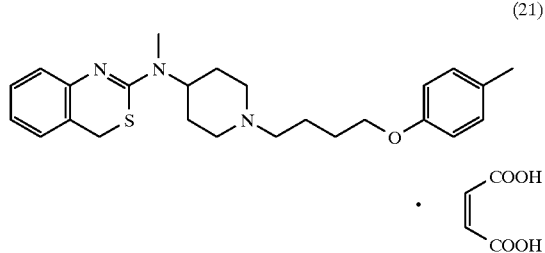

(21)

Empirical formula: $C_{29}H_{37}N_3O_5S$; Molecular mass: 539.66; Melting point: 144–6°; NMR (CDCl₃) δ: 1.7–2.15 (m, 6H); 2.28 (s, 3H); 2.2–2.5 (m, 2H); 2.87 (t, 2H); 3.07 (s, 3H); 3–3.3 (m, 2H); 3.55–3.75 (m, 2H); 3.86 (s, 2H); 3.97 (t, 2H); 4.8–5.15 (m, 1H); 6.28 (s, 2H); 6.76 (d, 2H); 6.9–7.15 (m, 5H); 7.15–7.35 (m, 1H); 10.5–13.5 (m, 2H).

EXAMPLE 22

N-Methyl-N-[1-[4-(4-methoxyphenoxy)butyl]piperid-4-yl]-4H-3,1-benzothiazin-2-armine hydrogen maleate (22).

Condensation of 1,4-dibromobutane with 4-methoxyphenol according to A. M. Ismaiel et al. (*J Med Chem* (1993) 36, 2519–25) gives an 82% yield of 1-(4-methoxyphenoxy)-4-bromobutane. By condensing 670 mg (2.58 mmol) of this derivative with 700 mg (2.35 mmol) of N-methyl-N-[4-piperidyl]-4H-3,1-benzothiazin-2-amine, obtained in Example 16-2, in 8 ml of dry DMF in the presence of 630 mg (5.8 mmol) of 98 $Na_2CO_3$/02 KI according to the procedure of Example 16-3, the compound of formula 22 is prepared in a yield of 58%:

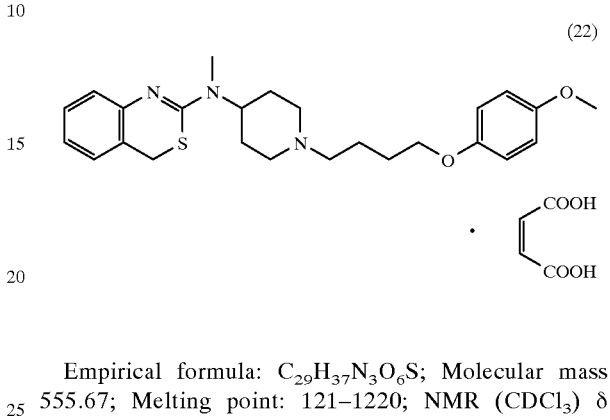

(22)

Empirical formula: $C_{29}H_{37}N_3O_6S$; Molecular mass: 555.67; Melting point: 121–1220; NMR (CDCl₃) δ: 1.7–2.15 (m, 6H); 2.15–2.55 (m, 2H); 2.7–3 (m, 2H); 3.07 (s, 3H); 3–3.3 (m, 2H); 3.55–3.82 (m, 2H); 3.76 (s, 3H); 3.86 (s, 2H); 3.94 (t, 2H); 4.85–5.2 (m, 1H); 6.29 (s, 2H); 6.82 (s, 4H); 6.94–7.17 (m, 3H); 7.2–7.4 (m, 1H); 11–13.5 (m, 2H).

EXAMPLE 23

(dl)-N-[1-[2-Hydroxy-3-(3,4-difluorophenoxy)propyl]-piperid-4-yl]-4H-3,1-benzothiazin-2-amine dihydrochloride (23).

23-1: 1-(3,4-Difluorophenoxy)-2,3-epoxypropane: condensation of 25 g (192 mmol) of 3,4-difluorophenol with 45.2 ml (576 mmol) of epichlorohydrin in 96 ml of 2N sodium hydroxide in the presence of 2 g of $Bu_4NHSO_4$ according to the process of W. S. Di Menna et al. (*J Med Chem* (1978) 21, 1073–6) gives 28.4 g (yield: 80%) of oil of formula 23-1:

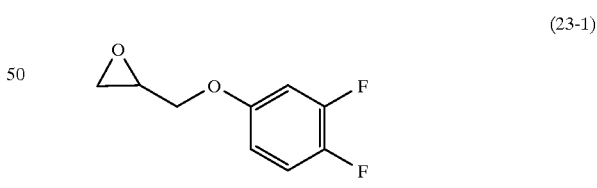

(23-1)

Empirical formula: $C_9H_8F_2O_2$; Molecular mass: 186.154; Boiling point: 104–105°/l mbar 23-2: 4-tert-Butoxycarbonylamino-1-[2-hydroxy-3-(3,4-difluorophenoxy)propyl]piperidine: starting with 7.5 g (37.4 mmol) of 4-tert-butoxycarbonylaminopiperidine prepared in Example 14-2 and by condensing them with 8.35 g (45 mmol) of the above epoxide in 75 ml of methanol according to the process described in Example 14-3, 16 g (yield: 83%) of the compound of formula 23-2 are obtained:

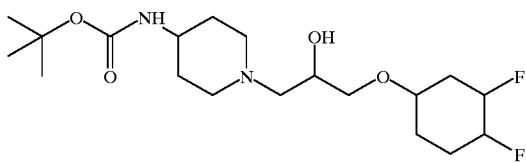

Empirical formula: $C_{19}H_{28}F_2N_2O_4$; Molecular mass: 386.43; Melting point: 99–100°;

23-3: 1-[2-Hydroxy-3-(3,4-difluorophenoxy)propyl]-4-piperidinamine: 10 g (26 mmol) of the above derivative are hydrolyzed with 75 ml of 3N hydrochloric acid according to the procedure of Example 14-4 to give 5.9 g (yield: 79%) of base of formula 23-3 which is used without further purification in the following step:

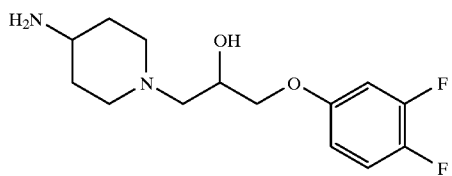

Empirical formula: $C_{14}H_{20}F_2N_2O_2$; Molecular mass: 286.32; Pale yellow oil.

23-4: (dl)-N-[1-[2-Hydroxy-3-(3,4-difluorophenoxy)-propyl]piperid-4-yl]-4H-3,1-benzothiazin-2-amine dihydrochloride: condensation of 530 mg (2.32 mmol) of 2-bromomethylphenyl isothiocyanate with 665 mg (2.32 mmol) of base 23-3 according to the process of Example 14-5 gives 675 mg (yield: 58%) of white crystals of formula 23:

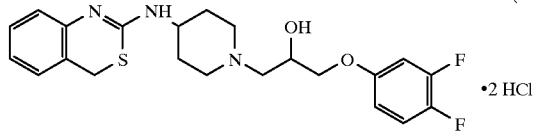

Empirical formula: $C_{22}H_{27}F_2Cl_2N_3O_2S$; Molecular mass: 506.43; Melting point: 250–251°; (Melting point of the base: 117–118°) NMR (DMSO $d_6$) δ: 1.9–2.4 (m, 4H); 2.9–3.85 (m, 4H); 3.85–4.1 (m, 3H); 4.25 (s, 2H); 4.3–4.55 (m, 2H); 4.6–5 (m, 1H); 5.8–6.3 (m, 1H); 6.75–6.9 (m, 1H); 7.05–7.55 (m, 5H); 7.8–8.1 (m, 1H); 10.7–11.2 (m, 2H); 12.5–13.5 (m, 1H).

EXAMPLE 24

N-Methyl-N-[1-[4-(4-fluorophenoxy)butyl]piperid-4-yl]-1,5-dihydro-2,4-benzothiazepin-3-amine dihydrogen fumarate hydrate (24).

24-1: 1-Pivaloyl-3-[1-[4-(4-fluorophenoxy)butyl]piperid-4-yl]-3-methylthiourea: a suspension of 1.73 g (17.8 mmol) of potassium thiocyanate in 100 ml of dry acetone is stirred on a bath of ice and then treated dropwise, at about 4°, with 2.2 ml (17.8 mmol) of pivaloyl chloride and stirring is continued for 3 h at the same temperature. 5 g (17.8 mmol) of N-methyl-N-[1-[4-(4-fluorophenoxy)butyl]piperidine-4-amine base are then introduced, after which the mixture is allowed to warm slowly to 25° overnight. The inorganic salt is removed by filtration and rinsed with a small amount of acetone and the filtrate is evaporated to dryness to give a yellow oil which is taken up in dichloromethane, washed with water, dried over sodium sulfate and evaporated to dryness. The residual oil, triturated from hexane, gives 7.3 g (yield: 95%) of off-white crystals of formula 24-1:

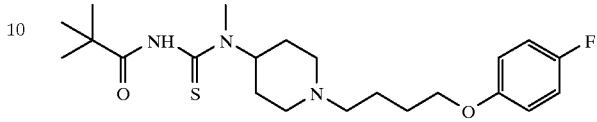

Empirical formula: $C_{22}H_{34}FN_3O_2S$; Molecular mass: 423.574; Melting point: 115°; NMR (CDCl$_3$) δ: 1.26 (s, 9H); 1.6–2.1 (m, 8H); 2.1–2.3 (m, 2H); 2.48 (t, 2H); 3 (s, 3H); 3–3.2 (m, 2H); 3.94 (t, 2H); 4.8–5.1 (m, 1H); 6.71–7 (m, 2H); 7–7.1 (m, 2H); 7.85 (s, 1H).

24-2: 1-Methyl-1-[1-[4-(4-fluorophenoxy)butyl]piperid-4-yl]thiourea: 5 g (11.32 mmol) of the above compound in 100 ml of concentrated hydrochloric acid are refluxed for one hour and the mixture is then cooled to 5° and basified on a bath of ice with 50% caustic soda. The base liberated is extracted with dichloromethane, washed with water and with brine and dried over sodium sulfate. The filtrate is evaporated to dryness to give an amber-colored oil which is triturated from hexane to give beige-colored crystals (m=3.1 g; yield: 77%) of formula 24-2:

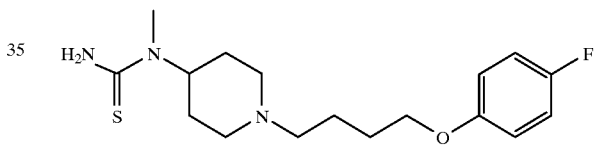

Empirical formula: $C_{17}H_{26}FN_3OS$; Molecular mass: 339.477; Melting point: 106–107°; NMR (CDCl$_3$) δ: 1.5–1.9 (m, 8H); 2.08 (td, 2H); 2.39 (t, 2H); 2.94 (s, 3H); 2.9–3.1 (m, 2H); 3.91 (t, 2H); 4.8–5.25 (m, 1H); 5.71 (s, 2H); 6.7–6.85 (m, 2H); 6.85–7.95 (m, 2H).

24-3: N-Methyl-N-[1-[4-(4-fluorophenoxy)butyl]piperid-4-yl]-1,5-dihydro-2,4-benzothiazepin-3-amine dihydrogen fumarate hydrate: a suspension of 1.56 g (14.7 mmol) of sodium carbonate in 100 ml of acetone is treated, under a stream of nitrogen, with 2.5 g (7.36 mmol) of the above compound and then with 1.95 g (7.36 mmol) of α,α'-dibromo-o-xylene. The mixture is refluxed for 4 h. After cooling to 25°, the inorganic salt is filtered off and the filtrate is evaporated to dryness. The residual orange-colored oil is purified by flash chromatography to give 2.06 g of orange-colored oil (yield: 64%) which is salified in the usual manner with two equivalents of fumaric acid to give compound 24 of formula:

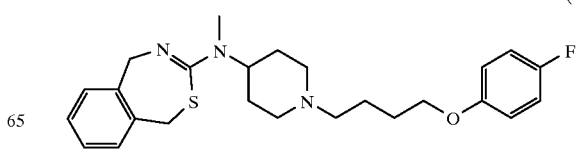

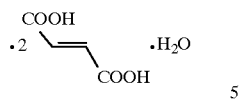

Empirical formula: $C_{33}H_{40}FN_3O_9S$, $H_2O$; Molecular mass: 691.75; Melting point: 141–143°; NMR (base) (CDCl$_3$) δ: 1.5–1.85 (m, 8H); 1.99 (td, 2H); 2.35 (t, 2H); 2.75 (s, 3H); 2.75–3.1 (m, 2H); 3.9 (t, 2A); 3.9–4.1 (m, 1H); 4.22 (s, 2H); 4.76 (s, 2H); 6.8–6.87 (m, 2H); 6.87–7.05 (m, 2H); 7.1–74 (m, 4H).

EXAMPLE 25

N-Methyl-N-[1-[4-(3,4-difluorophenoxy)butyl]piperid-4-yl]-1,5-dihydro-2,4-benzothiazepin-3-amine dihydrogen fumarate hydrate (25).

25-1: 1-Pivaloyl-3-[1-[4-(3,4-difluorophenoxy)butyl]-piperid-4-yl]-3-methylthiourea: working as described in Example 24-1, but starting with 5 g (16.7 mmol) of N-methyl-1-[4-(3,4-difluorophenoxy)butyl]-4-piperidinamine, 6.3 g (yield: 85%) of the compound of formula 25-1 are prepared:

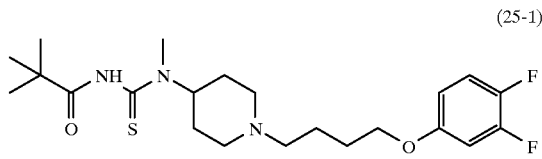

Empirical formula: $C_{22}H_{33}F_2N_3O_2S$; Molecular mass: 441.564; Melting point: 87°; NMR (CDCl$_3$) δ: 1.25 (s, 9H); 1.5–2.2 (m, 10H); 2.4 (t, 2H); 2.97 (s, 3H); 2.95–3.1 (m, 2H); 3.90 (t, 2H); 4.75–5.05 (m, 1H); 6.5–6.63 (m, 1H); 6.69 (qd, 1H); 7.03 (q, 1H); 7.83 (s, 1H).

25-2: 1-Methyl-1-[1-[4-(3,4-difluorophenoxy)butyl]-piperid-4-yl]thiourea: by hydrolyzing the above compound according to the process of Example 24-2, the compound of formula 25-2 is prepared in a yield of 89%:

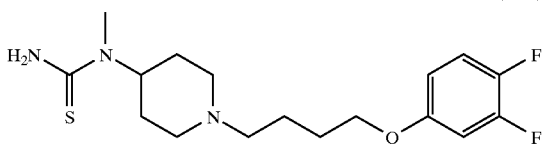

Empirical formula: $C_{17}H_{25}F_2N_3OS$; Molecular mass: 357.454; Melting point: 81° C.; NM (CDCl$_3$) δ: 1.5–1.9 (m, 8H); 2.1 (qd, 2H); 2.39 (t, 2H); 2.95 (s, 3H); 2.9–3.1 (m, 2H); 3.9 (t, 2H); 4.85–5.3 (m, 1H); 5.72 (s, 2H); 6.48–6.61 (m, 1H); 6.68 (qd, 1H); 7.03 (q, 1H).

25-3: N-Methyl-N-[1-[4-(3,4-difluorophenoxy)butyl]-piperid-4-yl]-1,5-dihydro-2,4-benzothiazepin-3-amine dihydrogen fumarate hydrate (25): condensation of 3 g (8.4 mmol) of the above compound with 2.21 g (8.4 mmol) of α,α'-dibromo-o-xylene according to the description of Example 24-3 gives a 52% yield of the compound of formula 25:

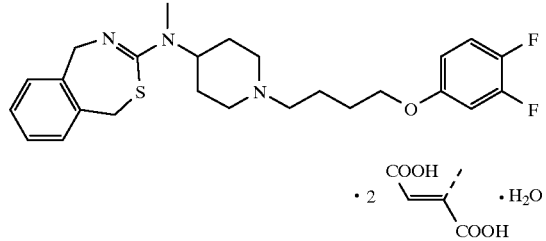

Empirical formula: $C_{33}H_{39}F_2N_3O_9S$, $H_2O$; Molecular mass: 709.763; Melting point: 122–124°; NMR of the base (CDCl$_3$) δ: 1.5–1.85 (m, 8H); 1.96 (td, 2H); 2.34 (t, 2H); 2.73 (s, 3H); 2.85–3.05 (m, 2H); 3.88 (t, 2H); 3.9–4.15 (m, 1H); 4.21 (s, 2H); 4.75 (s, 2H); 6.45–6.6 (m, 1H); 6.67 (qd, 1H); 7.02 (q, 1H); 7.12–7.35 (m, 4H).

EXAMPLE 26

6,7-Dimethoxy-N-[1-[3-(4-fluorophenoxy) propyl] piperid-4-yl]-4H-3,1-benzothiazin-2-amine hemifumarate (26).

26-1: 1-[3-(4-fluorophenoxy)propyl]piperid-4-yl isothiocyanate: a solution of 6 g (23.7 mmol) of 1-[3-[4-fluorophenoxy)propyl]-4-piperidinamine base (cf. Example 5) in 60 ml of dry DMF is added dropwise, under a stream of nitrogen, to a solution of 4.31 g (24.2 mmol) of thiocarbonyldiimidazole in 40 ml of dry DMF cooled on a bath of ice. After stirring for 30 minutes at 0°, the mixture is diluted in 750 ml of cold water and extracted with ethyl acetate. The organic phase is washed with brine, dried over sodium sulfate and evaporated to dryness to give 6.65 g (yield: 94%) of an amber-colored oil of formula 26-1:

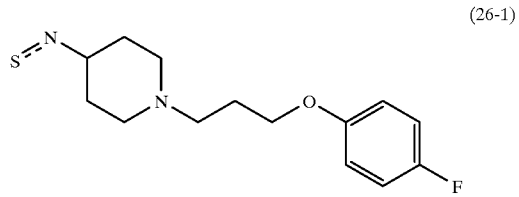

Empirical formula: $C_{15}H_{19}FN_2OS$; Molecular mass: 294.38; Amber-colored oil. IR (NaCl slides) υ: (N=C=S) 2107 cm$^{-1}$.

26-2: 1-[1-[3-[4-fluorophenoxy)propyl]piperid-4-yl]-3-(2-hydroxymethyl-4,5-dimethoxyphenyl) thiourea: starting-with 2.59 g (8.8 mmol) of the above derivative and by condensing them with 1.47 g of 2-amino-4,5-dimethoxybenzyl alcohol (prepared in Example 18-1) according to the process described in Example 17-2, beige-colored crystals of structure 26-2 are prepared in a yield of 84%:

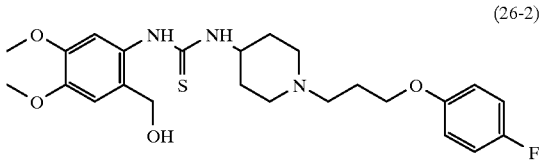

Empirical formula: $C_{24}H_{32}FN_3O_4S$; Molecular mass: 477.58; Melting point: 146°; NMR (DMSO d$_6$) δ: 1.3–1.65 (m, 2H); 1.7–2.1 (m, 6H); 2.4 (t, 2H); 2.7–2.95 (m, 2H); 3.71

(s, 3H); 3.77 (s, 3H); 3.96 (t, 2H); 3.9–4.3 (m, 1H); 4.36 (d, 2H); 5.08 (t, 1H); 6.8–7.2 (m, 6H); 7.3–7.6 (m, 1H); 8.82 (s, 1H).

26-3: 6,7-Dimethoxy-N-[1-[3-(4-fluorophenoxy)propyl]-piperid-4-yl]-4H-3,1-benzothiazin-2-amine hemifumarate: by cyclization of 3 g (6.38 mmol) of compound 26-2 above according to the process of Example 17-3, the compound of formula 26 is obtained by salifying with fumaric acid:

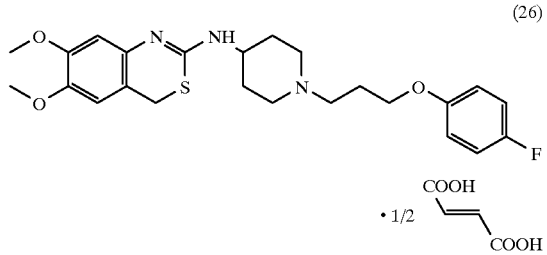
(26)

Empirical formula: $C_{26}H_{32}FN_3O_5S$; Molecular mass: 517.60; Melting point: 190–191°; NMR (DMSO $d_6$) δ: 1.35–1.7 (m, 2H); 1.7–2.05 (m, 4H); 2.1–2.35 (m, 2H); 2.56 (t, 2H); 2.8–3.1 (m, 2H); 3.7 (s, 3H); 3.72 (s, 3H); 3.84 (s, 2H); 3.98 (t, 2H); 3.7–4.5 (m, 2H); 6.50 (s, 1H); 6.55 (s, 1H); 6.75 (s, 1H); 6.85–7.05 (m, 2H); 7.05–7.25 (m, 2H); 9.5–12 (m, 1H).

EXAMPLE 27

N-[1-[4-(4-Fluorophenoxy)butyl]piperid-4-yl]-4H-3,1-benzoxazin-2-amine dihydrochloride (27).

27-1: 1-[1-[4-(4-Fluorophenoxy)butyl]piperid-4-yl]-3-(2-hydroxymethylphenyl)urea: a solution of 754 mg (2.54 mmol) of triphosgene in 50 ml of dry $CH_2Cl_2$ is cooled to 0° under a stream of nitrogen and treated dropwise with a solution of 1.88 g (7.6 mmol) of 1-[4-(4-fluorophenoxy)butyl]-4-piperidinamine and 1.08 ml (7.76 mmol) of triethylamine in 25 ml of $CH_2Cl_2$. After stirring for 5 minutes at 0° the mixture is allowed to warm to 25° over 2 h. The intermediate reaction product formed is not isolated and the above solution is treated dropwise with a solution of 869 mg (7.06 mmol) of 2-aminobenzyl alcohol and 0.98 ml (7.06 mmol) of triethylamine in 25 ml of $CH_2Cl_2$. After stirring overnight at 25°, the mixture is diluted with $CH_2Cl_2$ and washed with water and with brine and dried over sodium sulfate. After removal of the inorganic salt and evaporation to dryness, an oil is recovered which, when triturated from isopropyl ether, gives 2.1 g (yield: 72%) of beige-colored crystals of formula 27-1:

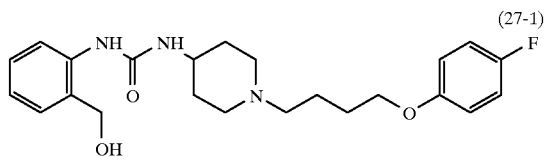
(27-1)

Empirical formula: $C_{23}H_{30}FN_3O_3$; Molecular mass: 415.49; Melting point: 145–146°; NMR (DMSO $d_6$) δ: 1.2–2.15 (m, 10H); 2.33 (t, 2H); 2.6–2.9 (m, 2H); 3.3–3.55 (m, 1H); 3.96 (t, 2H); 4.45 (d, 2H); 5.28 (t, 1H); 6.7–7 (m, 4H); 7–7.4 (m, 4H); 7.77 (s, 1H); 7.86 (d, 1H).

27-2: N-[1-[4-(4-Fluorophenoxy)butyl]piperid-4-yl]-4H-3,1-benzoxazin-2-amine dihydrochloride: a mixture of 1.4 g (3.37 mmol) of the above compound in 7 ml of concentrated hydrochloric acid is heated at 40–50° for 10 minutes and is then left overnight at 25°. The mixture is evaporated to dryness, taken up in isopropyl alcohol, evaporated to dryness, triturated from isopropyl alcohol, filtered and recrystallized from aqueous isopropanol to give 910 mg (yield: 58%) of white crystals of formula 27:

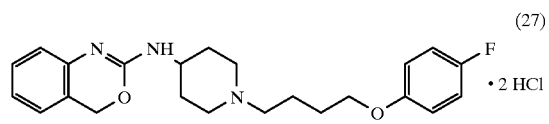
(27)

Empirical formula: $C_{23}H_{30}Cl_2FN_3O_2$; Molecular mass: 470.396; Melting point: 208° (dec.) NMR ($D_2O$) δ: 1.7–2.1 (m, 6H); 2.1–2.5 (m, 2H); 3–3.45 (m, 4H); 3.45–3.8 (m, 2H); 4.08 (t, 2H); 4–4.4 (m, 1H); 5.61 (s, 2H); 6.9–7.25 (m, 5H); 7.25–7.5 (m, 3H).

EXAMPLE 28

6,7-Dimethoxy-N-[1-[4-(4-fluorophenoxy)butyl]piperid-4-yl]-4H-3,1-benzothiazin-2-amine hemifumarate (28).

28-1: 1-[1-[4-(4-Fluorophenoxy)butyl]piperid-4-yl]-3-(2-hydroxymethyl-4,5-dimethoxyphenyl) thiourea: condensation of 2.40 g (6.6 mmol) of 1-[4-(4-fluorophenoxy)butyl]-piperid-4-yl isothiocyanate, prepared in Example 17-1, with 1.10 g of 4,5-dimethoxy-2-aminobenzyl alcohol, prepared in Example 18-1, in 30 ml of dioxane according to the process described in Example 17-2 gives 2.37 g (yield: 80%) of compound of formula 28-1:

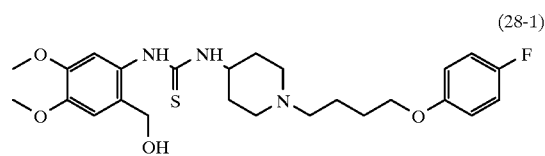
(28-1)

Empirical formula: $C_{25}H_{34}FN_3O_4S$; Molecular mass: 491.60; Melting point: 160°; NMR (DMSO $d_6$) δ: 1.25–2.15 (m, 10H); 2.27 (t, 2H); 2.65–2.9 (m, 2H); 3.68 (s, 3H); 3.73 (s, 3H); 3.91 (t, 2H); 3.9–4.2 (m, 1H); 4.32 (d, 2H); 5.05 (t, 1H); 6.81 (s, 1H); 6.8–7.2 (m, 5H); 7.2–7.6 (m, 1H); 8.79 (s, 1H).

28-2: 6,7-Dimethoxy-N-[1-[4-(4-fluorophenoxy)butyl]-piperid-4-yl]-4H-3,1-benzothiazin-2-amine hemifumarate: cyclization of 2.2 g (4.47 mmol) of the above compound in 10 ml of 12N HCl at 60° according to Example 17-3 gives 2.01 g (yield: 95%) of beige-colored crystals which, on salification with fumaric acid, give a 79% yield of the compound of formula 28:

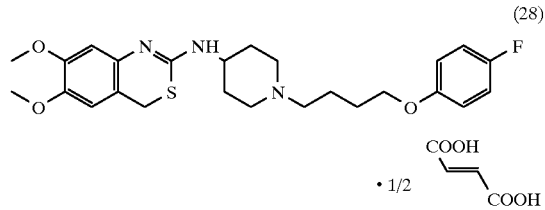
(28)

Empirical formula: $C_{27}H_{34}FN_3O_5S$; Molecular mass: 531.63; Melting point: 175°; (Melting point of the base: 126°) NMR (DMSO $d_6$) δ: 1.4–1.85 (m, 6); 1.85–2.1 (m, 2H); 2.23 (t, 2H); 2.9–3.15 (m, 2H); 3.71 (s, 3H); 3.73 (s, 3H); 3.85 (s, 2H); 3.96 (t, 2H); 6.51 (s, 1H); 6.55 (s, 1H); 6.76 (s, 1H); 6.85–7 (m, 2H); 7–7.3 (m, 2H); 9–13 (m, 2H).

EXAMPLE 29

6-Methyl-N-[1-[4-(4-fluorophenoxy)butyl]piperid-4-yl]-4H-3,1-benzothiazin-2-amine dihydrochloride hemi-hydrate (29).

29-1: 1-[1-[4-(4-Fluorophenoxy)butyl]piperid-4-yl]-3-[2-hydroxymethyl-4-methylphenyl]thiourea: reaction of 2.40 g (6.6 mmol) of 1-[4-(4-fluorophenoxy)butyl]piperid-4-yl isothiocyanate, prepared in Example 17-1, with 0.82 g (6 mmol) of 5-methyl-2-aminobenzyl alcohol, prepared in Example 20-1, according to the process of 17-2 gives 2.21 g (yield: 82%) of beige-colored crystals of formula 29-1:

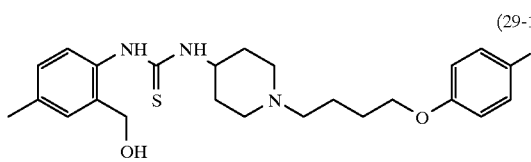

(29-1)

Empirical formula: $C_{24}H_{32}FN_3O_2S$; Molecular mass: 445.60; Melting point: 130°; NMR (DMSO $d_6$) δ: 1.3–2.1 (m, 10H); 2.27 (s, 3H); 2.2–2.4 (m, 2H); 2.65–2.9 (m, 2H); 3.92 (t, 2H); 3.8–4.2 (m, 1H); 4.38 (d, 2H); 5.13 (t, 1H); 6.8–7.3 (m, 7H); 7.4–7.7 (m, 1H); 8.78 (s, 1H)

29-2: 6-Methyl-N-[1-[4-(4-fluorophenoxy)butyl]piperid-4-yl]-4H-3,1-benzothiazin-2-amine dihydrochloride hemi-hydrate: by cyclization of 2.10 g (4.71 mmol) of the above compound in 15 ml of concentrated hydrochloric acid, the compound of formula 29 is prepared in a yield of 83%:

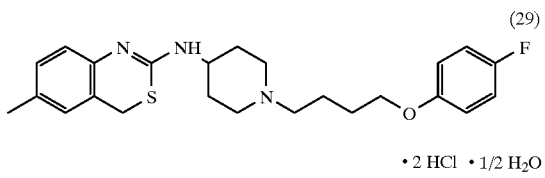

(29)

· 2 HCl · 1/2 H₂O

Empirical formula: $C_{24}H_{32}FN_3OS$; ½$H_2O$; Molecular mass: 509.49; Melting point: 242–244°; NMR (DMSO $d_6$) δ: 1.6–2.4 (m, 8H); 2.31 (s, 3H); 2.9–3,25 (m, 4H); 3.3–3.8 (m, 3H); 3.98 (t, 2H); 4.22 (s, 2H); 4.5–4.9 (s, 1H); 6.9–7.3 (m, 6H); 7.6–7.9 (m, 1H); 10.3–11.2 (m, 2H); 12.7–13.3 (m, 1H).

EXAMPLE 30

N,6-Dimethyl-N-[1-[4-(4-fluorophenoxy)butyl]piperid-4-yl)-4H-3,1-benzothiazin-2-amine hydrogen maleate (30).

A solution of 1.44 g (3.37 mmol) of 6-methyl-N-[1-[4-(4-fluorophenoxy)butyl]piperid-4-yl) -4H-3,1-benzothiazin-2-amine (Example 29) in 10 ml of dry DMF is cooled to 0° under a stream of nitrogen, followed by addition of 140 mg (3.54 mmol) of NaH (at 60%) portionwise; when the evolution of gas has ceased, 480 mg (210 μl or 3.37 mmol) of methyl iodide are added. After stirring for 30 minutes, the DMF is evaporated off under vacuum and the residue is taken up in 50 ml of $CH_2Cl_2$, washed with water and with brine and dried over sodium sulfate. After removal of the inorganic salt and evaporation to dryness, the residual oil is purified by flash chromatography, eluting with a 95 $CH_2Cl_2$/4.5 MeOH/0.5 $NH_4OH$ mixture to give 1.31 g (yield: 88%) of beige-colored crystals. The product is then salified with maleic acid in order to obtain 1.32 g (yield: 70%) of white crystals of formula 30:

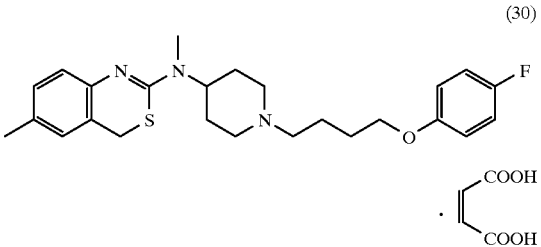

(30)

Empirical formula: $C_{29}H_{36}FN_3O_5S$; Molecular mass: 557.66; Melting point: 162°; (Melting point of the base: 83°) NMR (DMSO $d_6$) δ: 1.6–2.15 (m, 8H); 2.21 (s, 3H); 2.97 (s, 3H); 2.9–3.3 (m, 4H); 3.4–3.7 (m, 2H); 3.89 (s, 2H); 3.96 (t, 2H); 4.5–4.75 (m, 1H); 6.00 (s, 2H); 6.79 (d, 1H); 6.85–7.05 (m, 4H); 7.10 (t, 2H); 8.5–9.7 (m, 2H).

EXAMPLE 31

(dl)-N-methyl-N-[1-[2-hydroxy-3-(3,4-difluorophenoxy)-propyl]piperid-4-yl-4H-3,1-benzothiazin-2-amine dihydrochloride (31).

A solution of 572 mg (3.07 mmol) of 1-(3,4-difluorophenoxy)-2,3-epoxypropane (prepared in Example 23-1) and 670 mg (2.56 mmol) of N-methyl-N-(piperid-4-yl)-4H-3,1-benzothiazine-2-amine base (prepared in Example 16-2) in 6 ml of methanol is stirred overnight at 25°. The methanol is removed under vacuum and the oily residue is then purified by flash chromatography, eluting with a 97.4 $CH_2Cl_2$/2.3 MeOH/0.3 $NH_4OH$ mixture to give 1.58 g (yield: 64%) of pale yellow oil. The above base is converted into the hydrochloride in the usual manner from ethanol in order to give white crystals (m=1.18 g; yield: 42%) of formula 31:

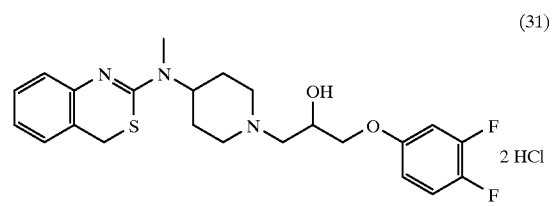

(31)

2 HCl

Empirical formula: $C_{23}H_{29}Cl_2F_2N_3O_2S$; Molecular mass: 520.45; Melting point: 196–198°; NMR (DMSO $d_6$) δ: 1.8–2.3 (m, 2H); 2.3–2.75 (m, 2H); 3–3.8 (m, 10H); 3.99 (d, 2H); 4.31 (s, 2H); 4.28–5.2 (m, 2H); 6.7–6.9 (m, 1H); 6.9–7.45 (m, 5H); 7.5–7.9 (m, 1H); 10.4–11 (m, 1H); 11.3–14 (m, 1H).

EXAMPLE 32

(S)-N-Methyl-N-[1-[2-hydroxy-3-(3,4-difluorophenoxy)-propyl]piperid-4-yl]-4H-3,1-benzothiazin-2-amine dihydrochloride (32).

32-1: (S)-1-(3,4-Difluorophenoxy)-2,3-epoxypropane: the process of J. M. Klunder et al. (*J. Med Chem* 1989, 54, 1295–1304) is adapted in order to prepare this chiral glycidyl ether. A solution of 10 g (76.8 mmol) of 3,4-difluorophenol in 100 ml of dry DMF is cooled to 0° and then treated, under a stream of nitrogen, with 6.14 g (153.7 mmol) of 60% sodium hydride. The stirring is continued for 20 minutes and the mixture is then treated with 17.5 g (76.8 mmol) of (S)-glycidyl tosylate and stirring is continued for 6 h at 25°. The reaction mixture is hydrolyzed from 600 ml of ice-cold water and is extracted with toluene, washed with water and with brine and dried over sodium sulfate. After removal of the inorganic salt and evaporation to dryness, the residual yellow oil (m=13.7 g; yield: 96%) is purified by flash chromatography, eluting with isopropyl ether. 10.1 g (yield: 70%) of compound of formula 32-1 are obtained, which product is used without further purification in the following step:

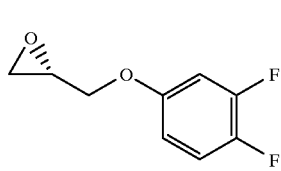

(32-1)

Empirical formula: $C_9H_8F_2O_2$; Molecular mass: 186.16; Colorless oil. $\alpha_D 24°=+10.90°$ (c=1% MeOH) NMR (CDCl$_3$) δ: 2.72 (dd, 1H); 2.89 (t, 1H); 3.24–3.45 (m, 1H); 3.84 (dd, 1H); 4.19 (dd, 1H); 6.5–6.9 (m, 2H); 7.03 (q, 1H)

32-2: (S)-N-Methyl-N-[1-[2-hydroxy-3-(3,4-difluorophenoxy)propyl]piperid-4-yl]-4H-3,1-benzothiazin-2-amine dihydrochloride: a solution of 890 mg (3.4 mmol) of N-methyl-N-(4-piperidinyl)-4H-3,1-benzothiazin-2-amine (cf: Example 16-2) in 8 ml of RP methanol is treated with 698 mg (3.75 mmol) of chiral epoxide 32-1 and stirred overnight at 25°. The solution is evaporated to dryness and the residual yellow oil is purified by flash chromatography, eluting with a 97.5 CH$_2$Cl$_2$/2.25 MeOH/0.25 NH$_4$OH mixture to give, after evaporation, a pale yellow oil (m=960 mg). This oil is converted into the hydrochloride with a solution of hydrochloric acid in ethanol, decolorized with animal charcoal and evaporated virtually to dryness. The hydrochloride precipitates on addition of ether and is recrystallized from alcohol to give 610 mg (yield: 35%) of cream-colored crystals of formula 32:

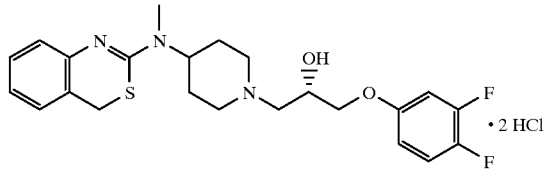

(32)

Empirical formula: $C_{23}H_{29}Cl_2F_2N_3O_2S$; Molecular mass: 520.46; αD=−10.8° (C=1%, MeOH)

BIOLOGICAL EXPERIMENTS

The compounds of the present invention of formula I and the therapeutically acceptable salts thereof have advantageous pharmacological properties. These derivatives are active on cardiomyocytes by inhibiting the diastolic contraction induced by veratrine in isolated rat left atrium. These compounds are also active in vivo during reinfusion ischemia in anaesthetized rabbits: they inhibit the electrical disturbances in the ECG caused by the reinfusion ischemia without any appreciable hemodynamic effect and are not cardiac depressors. Such compounds are useful for preventive or curative purposes in the treatment of coronaropathies and cardiac and cerebral ischemia in all their forms and in the treatment of atherosclerosis.

1°) Pharmacological study:

The experiments to which the chemical molecules which form the subject of the present invention were subjected made it possible to demonstrate an advantageous activity on the cardiovascular system both on "in vitro" and "in vivo" tests.

a) "in vitro" action

Inhibition of contraction of isolated rat left atrium by veratrine was carried out according to the technique of Le Grand et al. (*Naunyn—Schmiedeberg's Arch Phazmacol* (1993) 348 pp. 184–190). The results are given in the table below, in which the IC$_{50}$ values are expressed in micromoles for certain compounds, by way of non-limiting examples:

| Compound | Example No. 1 | R 56865* | Example No. 15 | Sabeluzole |
|---|---|---|---|---|
| IC$_{50}$ mmol | 0.15 | 0.25 | 0.32 | 5.1 | correspond to *N-(1-(4-(4-fluorophenoxy)butyl)piperid-4-yl)-N-methyl-2-benzothiazolamine and to **N-(1-(2-hydroxy-3 -(4-fluorophenoxy)propyl)piperid-4-yl)-N-methyl-2-benzothiazolamine cited in patent EP 0,184,257 and under development. The compounds of the present invention are not negative inotropes at a dose of 10 μM.

b) "in vivo" activity

Compounds of the present invention are also active via the venous route in the test of reinfusion ischemia in anaesthetized rabbits according to the method of Verscheure et al. (*Fundam Clin Pharmacol* (1993) 7, 385). The results for the compounds of Examples 1, 2, 11 and 15 are given in the table below by way of non-limiting example:

| Product No. or control | Dose mg/kg iv | % inhibition ST segment | Number of arrythmias under reinfusion | % heart rate variation | % arterial pressure variation |
|---|---|---|---|---|---|
| 1 | 0.16 | 76 | 3/5 | +3 | +6 |
| 2 | 0.16 | 76 | 1/5 | −3 | +4 |
| 11 | 0.16 | 71 | 1/5 | −1 | +3 |
| Atenolol | 0.16 | 64 | 4/6 | −13 | −9 |
| Diltiazem | 0.16 | 61 | 0/6 | −5 | −27 |
| 15 | 0.16 | 90 | 1/5 | 0 | +5 |
| Sabeluzole | 0.16 | 84 | 1/5 | −5 | 2 |

2°) Therapeutic applications:

The compounds of the present invention and the therapeutically acceptable salts thereof are useful as drugs. These compounds are more particularly suitable in cardiology in the prophylactic treatment of cardiovascular diseases such as:

myocardial ischemia and coronaropathies and more particularly in attacks:
of chronic stable angina,
of unstable angina and of Prinzmetal's angina,
silent ischemia, and in the prevention of reocclusion, restenosis and reinfarction.
cerebral ischemia, and more specifically in:
strokes,
transitory ischemic attacks,
neurodegenerative diseases,
and, lastly, in atherosclerosis.

These compounds can be administered orally, parenterally or rectally; each dose consists of an inert adjuvant which assists in the preparation, it being possible for the absorption of the drug and of the active principle also to be combined with another. These drugs can be presented in solid form (tablets or gelatin capsules) or liquid forms to be prepared at the time of use (suspensions, emulsions, syrups, solutions or the like) or suppositories. The active principle is administered at an average dose of between 0.1 and 10 mg/kg of bodyweight. Two preparations are given by way of non-limiting example. The ingredients, along with others that are therapeutically acceptable, can be introduced in other proportions without modifying the scope of the invention.

EXAMPLE 33
Injectable solution to be prepared at the time of use.

| 1°) A sterile bottle made of inactinic glass, for an injectable preparation, containing: | |
|---|---|
| N-methyl-N-[1-[4-(3,4-difluorophenoxy)butyl]-piperid-4-yl]-4H-3,1-benzothiazin-2-amine hydrogen maleate | 10 mg |
| 2°) A sterile glass vial of solvent containing: | |
| propylene glycol | 100 mg |
| anhydrous dextrose | 50 mg |
| sterile distilled water q.s. | 2 ml |

EXAMPLE 34
Tablets

| N-Methyl-N-[1-[4-(3,4-difluorophenoxy)butyl]-piperid-4-yl]-4H-3,1-benzothiazin-2-amine hydrogen maleate | 40 mg |
|---|---|
| Lactose hydrate | 100 mg |
| Microcrystalline cellulose | 25 mg |
| Carboxymethyl cellulose, sodium salt | 3 mg |
| Magnesium stearate | 2 mg |
| Corn starch | 20 mg |
| Talc | 3 mg |
| Polyvinylpyrrolidone | 7 mg |
| Total weight | 200 mg |

Splittable tablets to be stored away from heat and humidity.

EXAMPLE 35
(S) -N-Methyl-N-E[1-[2-hydroxy-3-(3,4-difluorophenoxy)-propyl]piperid-4-yl]-4H-3,1-benzothiazin-2-amine hydrogen maleate (35).

Working as described in Example 32, but salifying with one equivalent of maleic acid, off-white crystals of formula 35 are prepared in a yield of 55%:

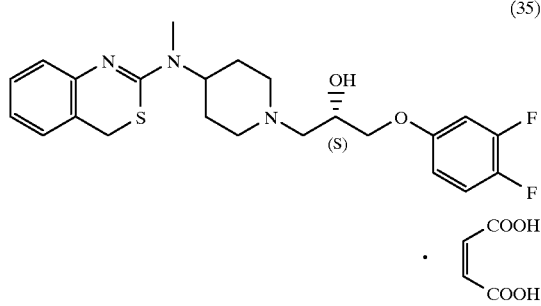

Empirical formula: $C_{27}H_{31}F_2N_3O_6S$; Molecular mass: 563.61; Melting point: 125–127°; (Melting point of the base: 89–90°) $\alpha_D^{26°}=-10.82°$ (c=1% MeOH) NMR (CDCl$_3$) δ: 1.9–2.1 (m, 2H); 2.2–2.5 (m, 2H); 2.9–3.4 (m, 4H); 3.1 (s, 3H); 3.7–4.2 (m, 6H); 4.4–4.6 (m, 1H); 4.9–5.1 (m, 1H); 6.3 (s, 2H); 6.6–6.9 (m, 2H) ; 7–7.4 (m, 5H); 8–13 (m, 3H)

EXAMPLE 36
N-Methyl-N-[1-[4-(4-fluorophenylthio)butyl]piperid-4-yl]-4H-3,1-benzothiazin-2-amine hydrogen maleate (36).

By condensation of 551 mg (2.09 mmol) of 4-fluoro-1-(4-bromobutylthio)benzene (prepared according to Example 22 in a yield of 41%) with 547 mg of N-methyl-N-(4-piperidinyl)-4H-3,1-benzothiazin-2-amine, obtained in Example 16-2 according to the procedure described in Example 16-3, the following compound of formula 36 is prepared in a yield of 51%:

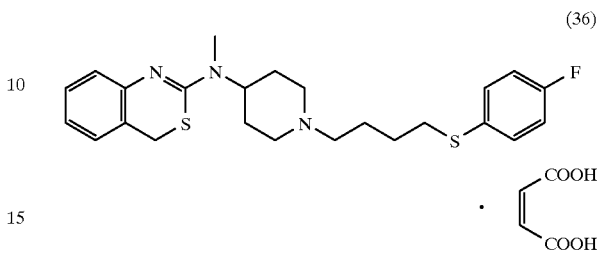

Empirical formula: $C_{28}H_{34}FN_3O_4S_2$; Molecular mass: 554.69; Melting point: 126–128°; NMR (DMSO d$_6$) δ: 1.5–1.8 (m, 2H); 1.8–2.1 (m, 4H); 2.2–2.5 (m, 2H); 2.5–3.2 (m, 6H); 3.08 (s, 3H); 2.65 (d, 2H); 3.88 (s, 2H); 4.8–5.1 (m, 1H); 6.3 (s, 2H); 6.9–7.2 (m, 5H); 7.2–7.5 (m, 3H); 9–12 (m, 2H).

EXAMPLE 37
N-Methyl-N-[1-[5-(4-fluorophenoxy)pentyl]piperid-4-yl]-4H-3,1-benzothiazin-2-amine hydrogen fumarate (37).

Working as described in Example 16-3, but starting with 520 mg of 4-fluoro-4-(5-bromopentyl)benzene and 520 mg of N-methyl-N-[4-piperidyl]-4H-3,1-benzothiazin-2-amine, and after salification with fumaric acid, white crystals of formula 37 are obtained (yield: 69%):

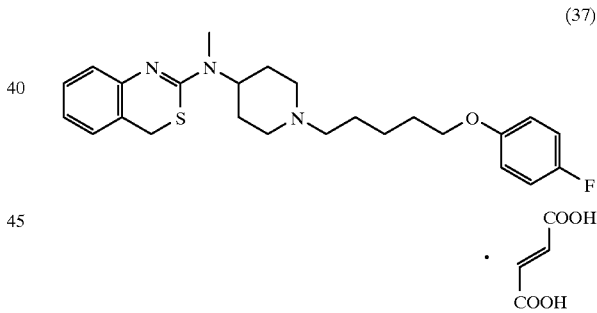

Empirical formula: $C_{29}H_{36}FN_3O_5S$; Molecular mass: 557.66; Melting point: 170–172°; NMR (DMSO d$_6$) δ: 1.3–1.70 (m, 6H); 1.75–2 (m, 2H); 2.3 (t, 2H); 2.4–2.6 (m, 2H); 2.99 (s, 3H); 3.11 (d, 2H); 3.8–4 (m, 2H); 3.92 (s, 2H); 4.2–4.5 (m, 1H); 6.55 (s, 2H); 6.8–7 (m, 4H); 7–7.2 (m, 4H); 8.5–12.5 (m, 2H).

EXAMPLE 38
N-Methyl-N-[1-[3-(4-fluorophenoxy)propyl]piperid-4-yl]-4H-3,1-benzothiazin-2-amine hydrogen fumarate (38).

Condensation of 600 mg (2.63 mmol) of 1-bromomethylphenyl isothiocyanate with 940 mg (2.63 mmol) of N-methyl-1-[3-(3,4-difluorophenoxy)propyl] piperid-4-yl amine according to the process of Example 1 leads to the compound of formula 38 in a yield of 61%:

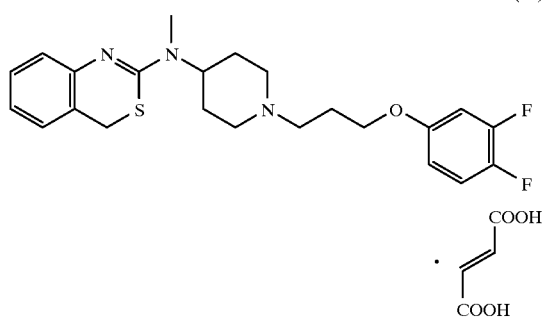

(38)

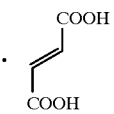

Empirical formula: $C_{27}H_{31}F_2N_3O_5S$; Molecular mass: 547.61; Melting point: 171–173°; NMR (DMSO $d_6$) δ: 1.5–1.7 (m, 2H); 1.7–2.1 (m, 4H); 2.26 (t, 2H); 2.6 (t, 2H); 3.01 (s, 3H); 3–3.3 (m, 2H); 3.92 (s, 2H); 3.99 (t, 2H); 4.2–4.5 (m, 1H); 6.57 (m, 2H); 6.65–7.5 (m, 1H); 6.92 (t, 2H); 6.95–7.2 (m, 3H); 3.32 (q, 1H); 8.5–12 (m, 2H).

EXAMPLE 39

N-Methyl-N-[1-[6-(4-fluorophenoxy)hexyl]piperid-4-yl]-4H-3,1-benzothiazin-2-amine hydrogen fumarate (39).

Using the process of Example 16-3 but starting with 550 mg of 4-fluoro-1-(6-bromohexyloxy)benzene and 520 mg (2 mmol) of N-methyl-N-[4-piperidyl]-4H-3,1-benzothiazin-2-amine, the compound of formula 39 is obtained in a yield of 68%:

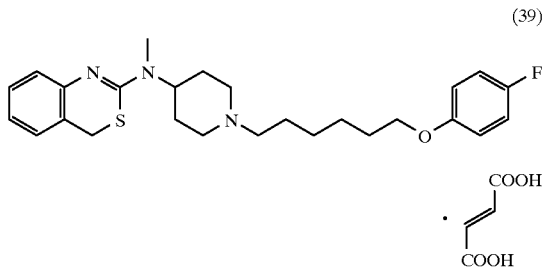

(39)

Empirical formula: $C_{30}H_{36}FN_3O_5S$; Molecular mass: 571.68; Melting point: 176–178°; NMR (DMSO $d_6$) δ: 1.2–2.1 (m, 10H); 2.34 (t, 2H); 2.45–2.55 (m, 2H); 3.03 (s, 3H); 3.05–3.3 (s, 2H); 3.8–4.1 (m, 2H); 3.95 (s, 2H); 4.25–4.6 (m, 1H); 6.58 (s, 2H); 6.85–7.05 (m, 4H); 7.1–7.3 (m, 4H); 9–12 (m, 2H).

EXAMPLE 40

N-Methyl-N-[1-[4-(3,4-dimethoxyphenoxy)butyl]piperid-4-yl-4H-3,1-benzothiazin-2-amine hydrogen fumarate (40).

By condensation of 720 mg (2.5 mmol) of 3,4-dimethoxy-1-(4-bromobutoxy)benzene with 650 mg (2.5 mmol) of N-methyl-N-[4-piperidyl]-4H-3,1-benzothiazin-2-amine according to Example 16-3, the compound of formula 40 is obtained in a yield of 75%:

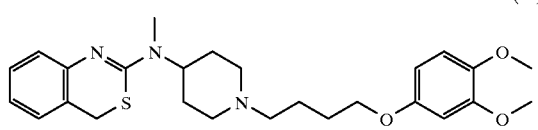

(40)

Empirical formula: $C_{30}H_{39}N_3O_7S$; Molecular mass: 585.69; Melting point: 172–175°; NMR (DMSO $d_6$) δ: 1.5–1.7 (m, 6H); 1.7–2.1 (m, 2H); 2.26 (t, 2H); 2.4–2.65 (m, 2H); 3 (s, 3H); 3.05–3.2 (m, 2H); 3.66 (s, 3H); 3.72 (s, 3H); 3.8–4 (m, 2H); 3.92 (s, 2H); 4.2–4.5 (m, 1H); 6.4 (dd, 1H); 6.54 (d, 1H); 6.57 (s, 2H); 6.8–7 (m, 3H); 7.05–7.25 (m, 2H); 8.5–12 (m, 2H).

EXAMPLE 41

N-Methyl-N-[1-[4-(2-methoxyphenoxy)butyl]piperid-4-yl]-4H-3,1-benzothiazin-2-amine hydrogen fumarate (41).

Reaction of 650 mg (2.5 mmol) of 2-methoxy-1-(4-bromobutoxy)benzene with 656 mg (2.5 mmol) of N-methyl-N-[4-piperidyl]-4H-3,1-benzothiazin-2-amine according to the process of Example 16-3 gives a 69% yield of beige-colored crystals of formula 41:

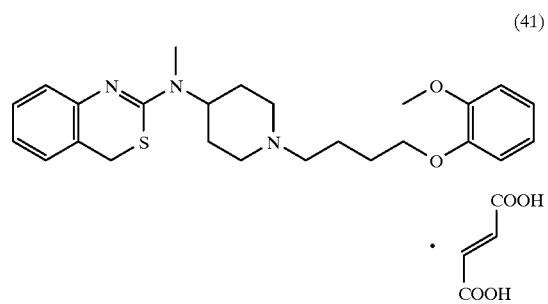

(41)

Empirical formula: $C_{29}H_{37}N_3O_6S$; Molecular mass: 555.66 Melting point: 172°; NMR (DMSO $d_6$) δ: 1.5–2.1 (m, 8H); 2.31 (t, 2H); 2.58 (t, 2H); 3.02 (s, 3H); 3–3.3 (m, 2H); 3.75 (s, 3H); 3.94 (s, 2H); 3.9–4.05 (m, 2H); 4.25–4.5 (m, 1H); 6.58 (s, 2H); 6.8–7.05 (m, 6H); 7.05–7.25 (m, 2H); 8–12 (m, 2H).

EXAMPLE 42

N-Methyl-N-[1-[4-(2, 3-dimethoxyphenoxy)butyl]piperid-4-yl]-4H-3,1-benzothiazin-2-amine hydrogen fumarate (42).

N-alkylation of 520 mg (2 mmol) of N-methyl-N-[4-piperidyl]-4H-3,1-benzothiazin-2-amine with 580 mg (2 mmol) of 2,3-dimethoxy-1-(4-bromobutoxy)benzene according to the procedure of Example 16-3 leads to the compound of formula 42 in a yield of 61%.

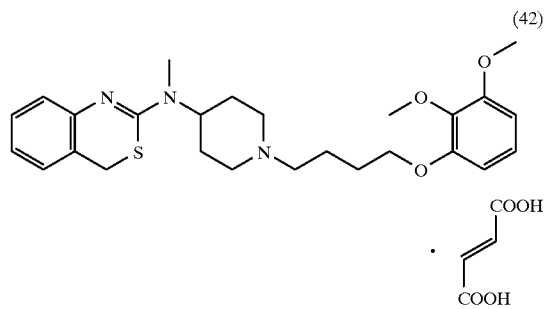

(42)

Empirical formula: $C_{30}H_{39}N_3O_7S$; Molecular mass: 585.70; Melting point: 146°; NMR (DMSO $d_6$) δ: 1.5–2.05

(m, 8H); 2.27 (t, 2H); 2.56 (t, 2H); 3 (s, 3H); 3–3.2 (m, 2H); 3.65 (s, 3H); 3.74 (s, 3H); 3.92 (s, 2H); 3.97 (t, 2H); 4.25–4.5 (m, 1H); 6.56 (s, 2H); 6.57–6.7 (m, 2H); 6.8–7 (m, 3H); 7.02–7.2 (m, 2H); 8.5–12 (m, 2H).

EXAMPLE 43

N-Methyl-N-[1-[4-(3, 5-dimethoxyphenoxy)butyl]piperid-4-yl]-4H-3,1-benzothiazin-2-amine hydrogen fumarate (43).

By condensing 775 mg (2.7 mmol) of 3,5-dimethoxy-1-(4-bromobutoxy)benzene with 700 mg (2.7 mmol) of N-methyl-N-[4-piperidyl]-4H-3,1-benzothiazin-2-amine, using the procedure described in Example 16-3, formula 43 is prepared in a yield of 58%:

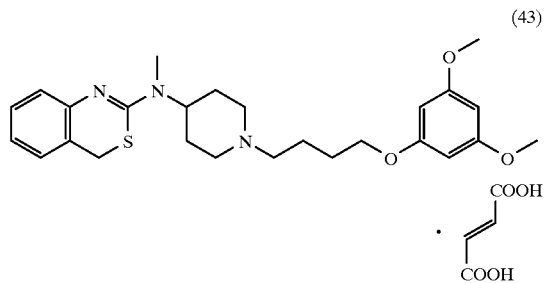

Empirical formula: $C_{30}H_{39}N_3O_7S$; Molecular mass: 585.70; Melting point: 173–174°; NMR (DMSO $d_6$) δ: 1.5–2.1 (m, 8H); 2.71 (t, 2H); 2.53 (t, 2H); 2.99 (s, 3H); 3–3.2 (m, 2H); 3.68 (s, 6H); 3.92 (s, 2H); 3.8–4 (m, 2H); 4.25–4.5 (m, 1H); 6.06 (s, 3H); 6.55 (s, 2H); 6.90 (t, 2H); 7.07–7.2 (m, 2H); 8–12 (m, 2H).

EXAMPLE 44

N-Methyl-N-[1-[4-(2,6-dimethoxyphenoxy)butyl]piperid-4-yl]-4H-3,1-benzothiazin-2-amine hydrogen fumarate (44).

Condensation of 700 mg (2.7 mmol) of N-methyl-N-[4-piperidyl]-4H-3,1-benzothiazin-2-amine with 775 mg (2.7 mmol) of 2,6-dimethoxy-1-(4-bromobutyl)benzene according to the procedure of Example 16-3 gives off-white crystals (yield: 63%) of formula 44:

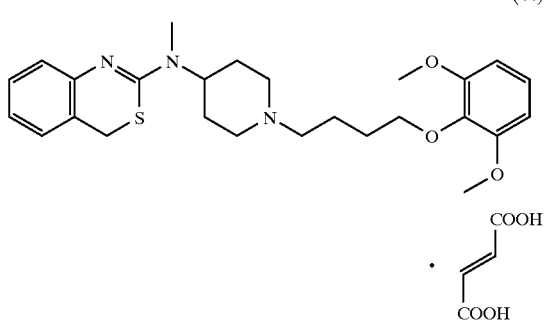

Empirical formula: $C_{30}H_{39}N_3O_3S$; Molecular mass: 585.70; Melting point: 155–156°; NMR (DMSO $d_6$) δ: 1.5–1.8 (m, 6H); 1.8–2.1 (m, 2H); 2.35 (t, 2H); 2.6 (t, 2H); 3.02 (s, 3H); 3.07–3.25 (m, 2H); 3.76 (s, 6H); 3.9 (t, 2H); 3.95 (s, 2H); 4.27–4.55 (m, 1H); 6.57 (s, 2H); 6.66 (d, 2H); 6.85–7.05 (m, 3H); 7.05–7.23 (m, 2H) ; 8–12 (m, 2H).

EXAMPLE 45

N-Methyl-N-[1-[4-(2,6-difluorophenoxy)butyl]piperid-4-yl]-4H-3,1-benzothiazin-2-amine hydrogen fumarate (45).

By reaction of 811 mg (3.06 mmol) of 2,6-difluoro-1-(4-bromobutoxy)benzene with 800 mg (3.06 mmol) of N-methyl-N-[4-piperidyl]-4H-3,1-benzothiazin-2-amine as described in Example 16-3, beige-colored crystals of formula 45 are obtained (yield: 59%):

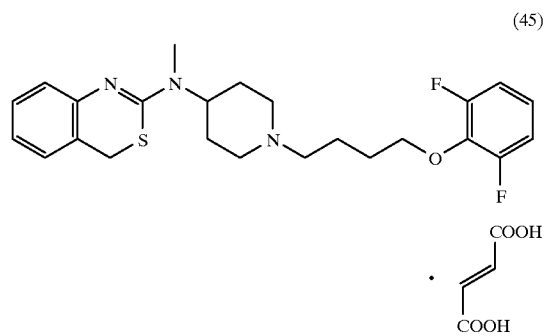

Empirical formula: $C_{28}H_{33}F_2N_3O_5S$; Molecular mass: 561.63; Melting point: 172–173°; NMR (DMSO $d_6$) δ: 1.5–2.05 (m, 8H); 2.27 (t, 2H); 2.54 (t, 2H); 3.01 (s, 3H); 3–3.2 (m, 2H); 3.94 (s, 2H); 4.11 (t, 2H); 4.2–4.5 (m, 1H); 6.58 (s, 2H); 6.93 (t, 2H); 7–7.25 (m, 5H); 8–12 (m, 2H).

EXAMPLE 46

N-Methyl-N-[1-[5-(3,4-difluorophenoxy)pentyl]piperid-4-yl]-4H-3,1-benzothiazin-2-amine hydrogen fumarate (46).

Using the procedure of Example 16-3 but starting with 800 mg of 3,4-difluoro-1-(5-bromopentyloxy)benzene and 800 mg of N-methyl-N-[4-piperidyl]-4H-3,1-benzothiazine and after salification with fumaric acid, the compound of formula 46 is prepared (yield: 48%):

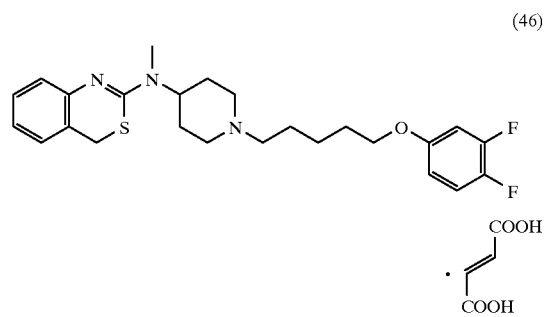

Empirical formula: $C_{29}H_{35}F_2N_3O_5S$; Molecular mass: 575.66; Melting point: 174–175°; NMR (DMSO $d_6$) δ: 1.3–2.05 (m, 10H); 2.32 (t, 2H); 2.4–2.62 (m, 2H); 3.02 (s, 3H); 3.05–3.22 (m, 2H); 3.94 (s, 2H); 3.96 (t, 2H); 4.25–4.5 (m, 1H); 6.58 (s, 2H); 66.65–6.85 (m, 1H); 6.85–7.45 (m, 6H) ; 8.5–12 (m, 2H).

EXAMPLE 47

N-Methyl-N-[1-[4-(3,5-difluorophenoxy)butyl]piperid-4-yl]-4H-3,1-benzothiazin-2-amine hydrogen fumarate (47).

Condensation of 800 mg (~3 mmol) of N-methyl-N-[4-piperidyl]-4H-3,1-benzothiazin-2-amine with 820 mg (~3 mmol) of 3,5-difluoro-1-(4-bromobutoxy)benzene according to the procedure of Example 16-3 gives 1.1 g of white crystals (yield: 66%) of formula 47:

(47)

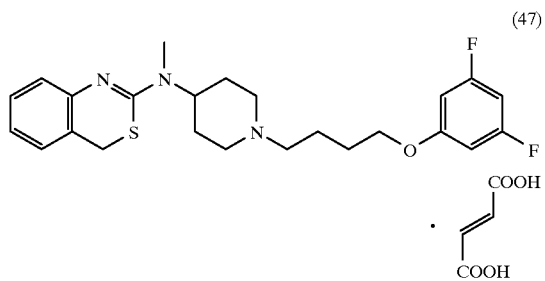

Empirical formula: $C_{28}H_{33}F_2N_3O_5S$; Molecular mass: 561.63; Melting point: 187–188°; NMR (DMSO $d_6$) δ: 1.5–2.05 (m, 8H); 2.32 (t, 2H); 2.58 (t, 2H); 3.02 (s, 3H); 3.03–3.23 (m, 2H); 3.94 (s, 2H); 4.02 (t, 2H); 4.25–4.5 (m, 1H); 6.6 (s, 2H); 6.63–6.85 (m, 3H); 6.94 (t, 2H); 7.05–7.25 (m, 2H); 8.5–12 (m, 2H).

EXAMPLE 48

N-Methyl-N-[1-[4-(2,4-difluorophenoxy)butyl]piperid-4-yl]-4H-3,1-benzothiazin-2-amine hydrogen fumarate (48).

Reaction of 1 g of 2,4-difluoro-1-(4-bromobutoxy)benzene with 990 mg of N-methyl-N-[4-piperidyl]-4H-3,1-benzothiazin-2-amine under the conditions of Example 16-3 gives 1.3 g (yield: 62%) of white crystals of formula 48:

(48)

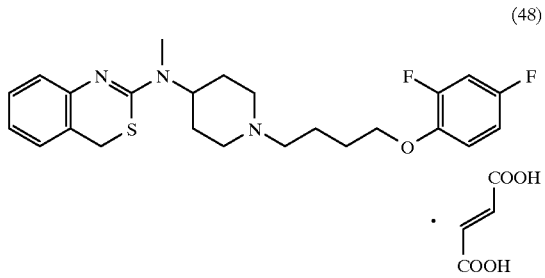

Empirical formula: $C_{28}H_{33}F_2N_3O_5S$; Molecular mass: 561.63; Melting point: 186°; NMR (DMSO $d_6$) δ: 1.5–2.1 (m, 8H); 2.34 (t, 2H); 2.58 (t, 2H); 2.99 (s, 3H); 3.02–3.24 (m, 2H); 3.92 (s, 2H); 4.02 (t, 2H); 4.25–4.5 (m, 1H); 6.55 (s, 2H); 6.75–7.05 (m, 3H); 7.05–7.35 (m, 4H); 8.5–12 (m, 2H).

EXAMPLE 49

N-Methyl-N-[1-[4-(2,5-difluorophenoxy)butyl]piperid-4-yl]-4H-3,1-benzothiazin-2-amine hydrogen fumarate (49).

Working as described in Example 16-3 but starting with 436 mg (1.64 mmol) of 2,5-difluoro-1-(4-bromobutoxy)-benzene, the compound of formula 49 is prepared in a yield of 55%:

(49)

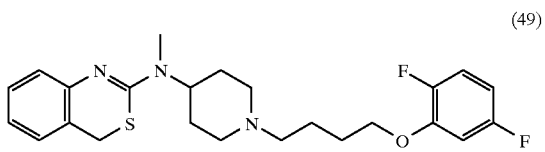

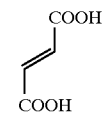

Empirical formula: $C_{28}H_{33}F_2N_3O_5S$; Molecular mass: 561.63; Melting point: 179°; NMR (DMSO $d_6$) δ: 1.5–2 (m, 8H); 2.14 (t, 2H); 2.35–2.55 (m, 2H); 3.02 (s, 3H); 3–3.15 (m, 2H); 3.94 (s, 2H); 4.08 (t, 2H); 4.15–4.45 (m, 1H); 6.58 (s, 2H); 6.65–6.82 (m, 1H); 6.82–7 (m, 2H); 7–7.35 (m, 4H); 8.5–12 (m, 2H).

EXAMPLE 50

N-Methyl-N-[1-[4-(3-fluoro-4-chlorophenoxy)butyl]piperid-4-yl]-4H-3,1-benzothiazin-2-amine hydrogen fumarate (50).

The action of 540 mg (1.9 mmol) of 3-fluoro-4-chloro-1-(4-bromobutoxy)benzene on 500 mg (1.9 mmol) of N-methyl-N-[4-piperidyl]-4H-3,1-benzothiazin-2-amine according to the description of Example 16-3 allows access to the compound of formula 50 in a yield of 53%:

(50)

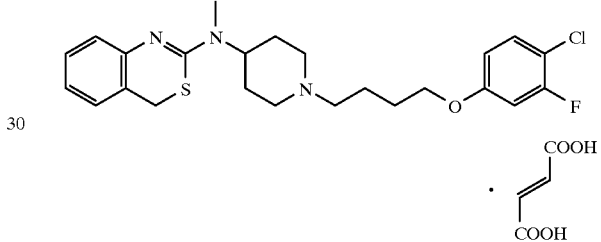

Empirical formula: $C_{28}H_{33}ClFN_3O_5S$; Molecular mass: 578.08; Melting point: 184°; NMR (DMSO $d_6$) δ: 1.5–2 (m, 8H); 2.16 (t, 2H); 2.3–2.52 (m, 2H); 3.01 (s, 3H); 2.95–3.15 (m, 2H); 3.93 (s, 2H); 4 (t, 2H); 4.2–4.45 (m, 1H); 6.59 (s, 2H); 6.65–7.25 (m, 6H); 7.44 (t, 1H); 8–13 (m, 2H)

EXAMPLE 51

N-Methyl-N-[1-[4-(2,3-difluorophenoxy)butyl]piperid-4-yl]-4H-3,1-benzothiazin-2-amine hydrogen fumarate (51).

Condensation of 610 mg (2.3 mmol) of 2,3-difluoro-1-(4-bromobutoxy)benzene with 600 mg (2.3 mmol) of N-methyl-N-[4-piperidyl]-4H-3,1-benzothiazin-2-amine under the conditions of Example 16-3 gives 970 mg (yield: 58%) of white crystals of formula 51:

(51)

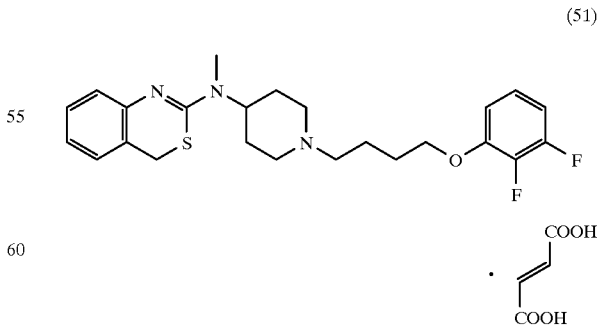

Empirical formula: $C_{28}H_{33}F_2N_3O_5S$; Molecular mass: 561.63; Melting point: 174°; NMR (DMSO $d_6$) δ: 1.45–2 (m, 8H); 2.15 (t, 2H); 2.3–2.55 (m, 2H); 3.01 (e, 3H); 3–3.15

(m, 2H); 3.94 (s, 2H); 4.11 (t, 2H); 4.2–4.45 (m, 1H); 6.58 (s, 2H); 6.8–7.25 (m, 7H); 8–12 (m, 3H).

EXAMPLE 52

N-Methyl-N-[1-[4-(3-chloro-4-fluorophenoxy)butyl] piperid-4-yl)-4H-3,1-benzothiazin-2-amine hydrogen fumarate (52).

N-Alkylation of 754 mg (2.68 mmol) of N-methyl-N-(4-piperidyl)-4H-3,1-benzothiazin-2-amine with 700 mg (2.68 mmol) of 3-chloro-4-fluoro-1-(4-bromobutoxy)benzene according to the process of Example 16-3 gives 1.21 g (yield: 78%) of white crystals of formula 52:

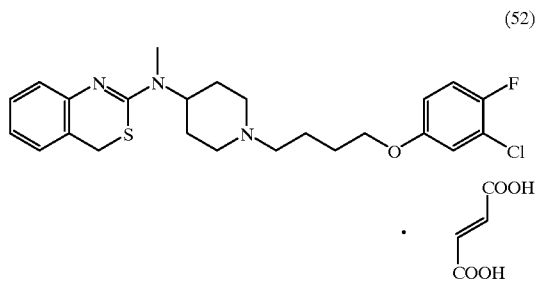

(52)

Empirical formula: $C_{28}H_{33}ClFN_3O_5S$; Molecular mass: 578.08; Melting point: 176°; NMR (DMSO $d_6$) δ: 1.5–2.1 (m, 8H); 2.3 (t, 2H); 2.56 (t, 2H); 3 (s, 3H); 3.05–3.2 (m, 2H); 3.92 (s, 2H); 3.98 (t, 2H); 4.25–4.5 (t, 1H); 6.56 (s, 2H); 6.82–7.02 (m, 3H); 7.05–7.21 (m, 3H); 7.31 (t, 1H); 8–13 (m, 2H).

EXAMPLE 53

N-Methyl-N-[1-[4-(3-fluorophenoxy) butyl]piperid-4-yl]-4H-3,1-benzothiazin-2-amine hydrogen fumarate (53).

Condensation of 600 mg (2.3 mmol) of N-methyl-N-(4-piperidyl)-4H-3,1-benzothiazin-2-amine with 570 mg (2.3 mmol) of 3-fluoro-1-(4-bromobutoxy)benzene under the conditions of Example 16-3 gives a 58% yield of the compound of formula 53:

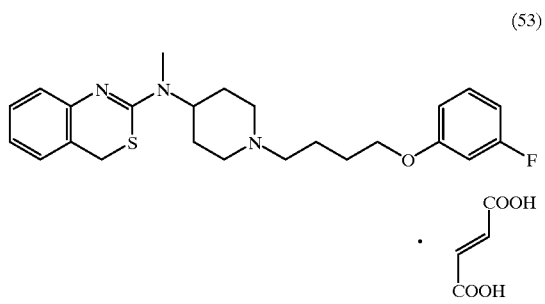

(53)

Empirical formula: $C_{28}H_{34}FN_3O_5S$; Molecular mass: 543.63; Melting point: 184°; NMR (DMSO $d_6$) δ: 1.5–2.05 (m, 8H); 2.26 (t, 2H); 2.53 (t, 2H); 3 (s, 3H); 3–3.22 (m, 2H); 3.92 (s, 2H); 3.98 (t, 2H); 4.25–4.5 (m, 1H); 6.56 (s, 2H); 6.65–7 (m, 4H); 7–7.4 (m, 4H); 8–13 (m, 2H).

EXAMPLE 54

N-Methyl-N-[1-[4-(3-methoxyphenoxy)butyl]piperid-4-yl]-4H-3,1-benzothiazin-2-amine hydrogen fumarate (54).

Using the procedure of Example 16-3 but starting with 655 mg (2.5 mmol) of 3-methoxy-1-(4-bromobutoxy) benzene, 980 mg (yield: 76%) of a white powder of formula 54 are prepared:

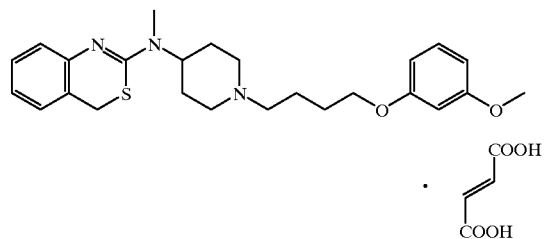

(54)

Empirical formula: $C_{29}H_{37}N_3O_6S$; Molecular mass: 555.67; Melting point: 165–166°; NMR (DMSO $d_6$) δ: 1.5–1.75 (m, 6H); 1.75–2.1 (m, 2H); 2.33 (t, 2H); 2.58 (t, 2H); 3 (s, 3H); 3.05–3.22 (m, 2H); 3.71 (s, 3H); 3.93 (s, 2H); 3.9–4.02 (m, 2H); 4.25–4.5 (m, 1H); 6.4–6.6 (m, 5H); 6.8–7 (m, 2H); 7–7.25 (m, 3H) ; 8–13 (m, 2H).

EXAMPLE 55

N-Methyl-N-[1-[4-(2-fluorophenoxy)butyl]piperid-4-yl]-4H-3,1-benzothiazin-2-amine hydrogen fumarate (55).

Application of the procedure 16-3 to 2-fluoro-1-(4-bromobutoxy)benzene (570 mg; 2.3 mmol) allows 810 mg (yield: 65%) of a white compound of formula 55 to be prepared:

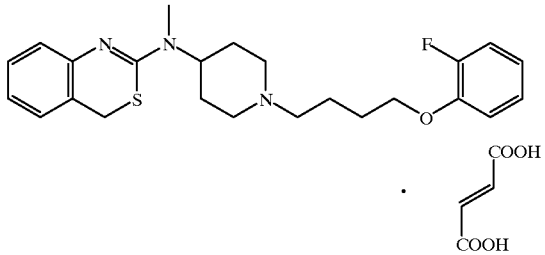

(55)

Empirical formula: $C_{28}H_{34}FN_3O_5S$; Molecular mass: 543.63; Melting point: 187°; NMR (DMSO $d_6$) δ: 1.5–2 (m, 8H); 2.18 (t, 2H); 2.35–2.6 (m, 2H); 2.9–3.15 (m, 2H); 2.99 (s, 3H); 3.92 (s, 2H); 4.05 (t, 2H); 4.25–4.5 (m, 1H); 6.58 (s, 2H); 6.82–7 (m, 3H) ; 7–7.3 (m, 5H) ; 8–13 (m, 2H).

EXAMPLE 56

N-Methyl-N-[1-[4-(2-methoxy-4-chlorophenoxy)butyl]-piperid-4-yl]-4H-3,1-benzothiazin-2-amine hydrogen fumarate (56).

Starting with 600 mg (2.3 mmol) of N-methyl-N-(4-piperidyl)-4H-1,3-benzothiazin-2-amine and by condensing them with 675 mg (2.3 mmol) of 2-methoxy-4-chloro-1-(4-bromobutoxy)benzene according to the process described in Example 16-3, the compound of formula 56 is prepared in a yield of 58%:

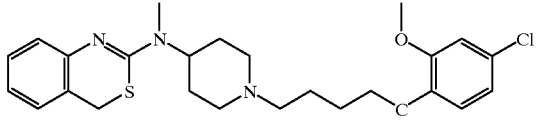

(56)

-continued

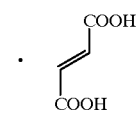

Empirical formula: $C_{29}H_{36}ClN_3O_6S$; Molecular mass: 590.14; Melting point: 184°; NMR (DMSO $d_6$) δ: 1.45–2.05 (m, 8H); 2.28 (t, 2H); 2.55 (t, 2H); 2.99 (s, 3H); 3–3.2 (m, 2H); 3.75 (s, 3H); 3.92 (s, 2H); 3.94 (t, 2H); 4.25–4.5 (m, 1H); 6.55 (s, 2H); 6.75–7.02 (m, 5H); 7.03–7.22 (m, 2H); 8–13 (m, 2H).

EXAMPLE 57
N-Methyl-N-[1-[4-(4-chlorophenoxy)butyl]piperid-4-yl]-4H-3,1-benzothiazin-2-amine hydrogen fumarate (57).

Condensation of 606 mg (2.3 mmol) of 4-chloro-1-(4-bromobutoxy)benzene with 600 mg (2.3 mmol) of N-methyl-N-(4-piperidyl) -4H-3,1-benzothiazinamine according to Example 16-3 gives 1.02 g (yield: 79%) of a white powder of formula 57:

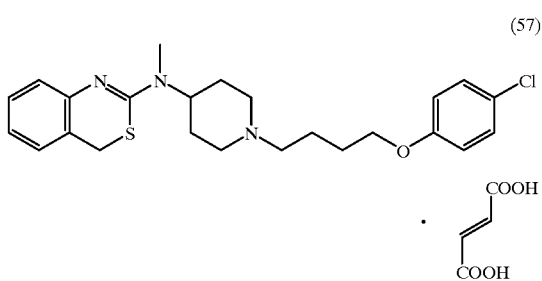

Empirical formula: $C_{28}H_{34}ClN_3O_5S$; Molecular mass: 560.12; Melting point: 188°; NMR (DMSO $d_6$) δ: 1.5–2.1 (m, 8H); 2.32 (t, 2H); 2.58 (t, 2H); 3.02 (s, 3H); 3–3.25 (m, 2H); 3.96 (s, 2H); 3.99 (t, 2H); 4.25–4.5 (m, 1H); 6.59 (s, 2H); 6.85–7.02 (m, 4H); 7.05–7.25 (m, 2H); 7.25–7.4 (m, 2H); 8–13 (m, 2H).

EXAMPLE 58
N-Methyl-N-[1-[5-(4-methoxyphenoxy)pentyl]piperid-4-yl]-4H-3,1-benzothiazin-2-amine hydrogen fumarate (58).

Adaptation of the process of Example 16-3 to 4-methoxy-1-(5-bromopentyloxy)benzene (630 mg; 2.3 mmol) allows the compound of formula 58 to be prepared in a yield of 51%:

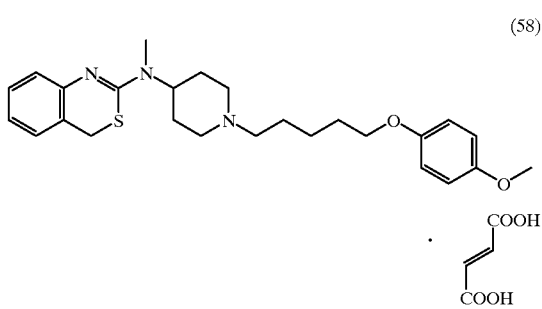

Empirical formula: $C_{30}H_{39}N_3O_6S$; Molecular mass: 569.72; Melting point: 187°; NMR (DMSO $d_6$) δ: 1.3–1.8 (m, 8H); 1.8–2.1 (m, 2H); 2.25–2.7 (m, 4H); 3.03 (s, 3H); 3.05–3.3 (m, 2H); 3.69 (s, 3H); 3.90 (t, 2H); 3.95 (s, 2H); 4.25–4.55 (m, 1H) ; 6.60 (s, 4H) ; 6.75–7.3 (m, 6H); 8–13 (m, 2H)

EXAMPLE 59
N-[1-[5-(3,4-Difluorophenoxy)pentyl]piperid-4-yl]-4H-3,1-benzothiazin-2-amine dihydrogen fumarate (59).

By condensation of 732 mg (2.7 mmol) of 3,4-difluoro-1-(5-bromopentyloxy)benzene with 636 mg (2.6 mmol) of N-(4-piperidyl)-4H-3,1-benzothiazin-2-amine according to the procedure 16-3, the compound of formula 59 is obtained in a yield of 51%:

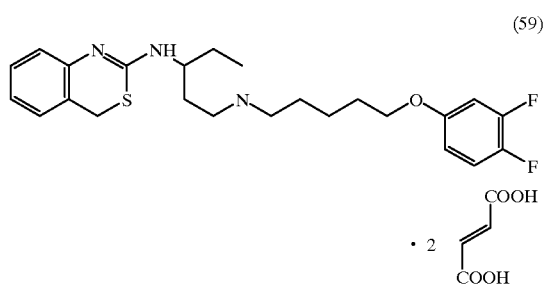

Empirical formula: $C_{32}H_{37}F_2N_3O_9S$; Molecular mass: 677.70; Melting point: 185–186°; NMR (DMSO $d_6$) δ: 1.27–1.82 (m, 8H); 1.9–2.15 (m, 2H); 2.55–2.85 (m, 4H); 3.15–3.32 (m, 2H); 3.92 (s, 2H); 3.96 (t, 2H); 3.95–4.15 (m, 1H); 6.57 (s, 4H); 6.65–7.45 (m, 7H); 8–14 (m, 5H)

EXAMPLE 60
N-[1-[5-(4-Fluorophenoxy)pentyl]piperid-4-yl]-4H-3,1-benzothiazin-2-amine dihydrogen fumarate (60).

Application of the procedure of Example 16-3 to 700 mg of N-(4-piperidyl)-4H-3,1-benzothiazin-2-amine and 776 mg (2.97 mmol) of 4-fluoro-1-(5-bromopentyloxy)benzene allows the compound of formula 60 to be prepared in a yield of 45%:

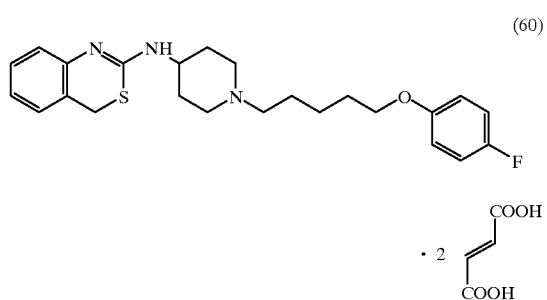

Empirical formula: $C_{32}H_{38}FN_3O_9S$; Molecular mass: 659.71; Melting point: 185–186°; NMR (DMSO $d_6$) δ: 1.25–1.8 (m, 8H); 1.85–2.1 (m, 2H); 2.5–2.85 (m, 4H); 3.1–3.3 (m, 2H); 3.88 (s, 2H); 3.90 (t, 2H); 3.95–4.15 (m, 1H); 6.54 (s, 4H); 6.78–7 (m, 4H) ; 7–7.22 (m, 4H) ; 7–8 (m, 1H); 8–14 (m, 4H)

EXAMPLE 61
(R)-N-Methyl-N-[1-[2-hydroxy-3-(3,4-difluorophenoxy)-propyl]piperid-4-yl]-4H-3,1-benzothiazin-2-amine hydrogen fumarate (61).

61-1: (R)-1-(3,4-Difluorophenoxy-2,3-epoxypropane Using the procedure of Example 32-1 but starting with 3.2 g (12.34 mmol) of R-glycidyl 3-nitrobenzenesulfonate and by condensing them with 1.69 g (13 mmol) of 3,4-difluorophenol, a straw-yellow colored oil of formula 61-1 is recovered (yield: 82%):

(61-1)

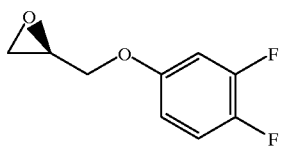

Empirical formula: $C_9H_8F_2O_2$; Molecular mass: 186.15; $\alpha_D^{24°} = -9.79°$ (c: 2.3%, MeOH);

61-2: (R)-N-Methyl-N-[1-(2-hydroxy-3-(3,4-difluorophenoxy)propyl]piperid-4-yl] -4H-3,1-benzothiazin-2-amine hydrogen fumarate. Working as described in Example 32-2 but by condensing 1.2 g (4.6 mmol) of the above (R) epoxide with 900 mg (4.83 mmol) of N-methyl-N-[4-piperidyl]-4H-3,1-benzothiazin-2-amine, the compound of formula 61 is prepared (yield: 48%):

(61)

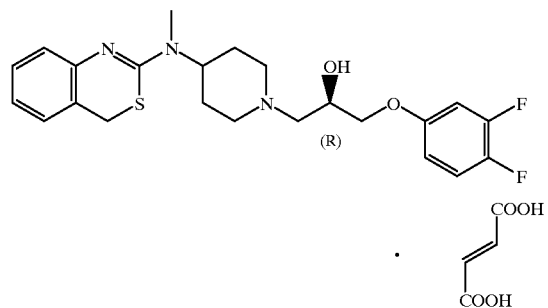

Empirical formula: $C_{27}H_{31}F_2N_3O_6S$; Molecular mass: 563.60; Melting point: 153–4°; $\alpha_D^{24°} = +8.05°$ (c: 1%, MeOH); e.e. $\geq 98\%$ (HPLC) NMR (DMSO $d_6$) δ: 1.5–1.7 (m, 2H); 1.7–2.05 (m, 2H); 2.35 (t, 2H); 2.5–2.7 (m, 2H); 3.01 (s, 3H); 2.95–3.2 (m, 2H); 3.92 (s, 2H); 3.75–4.05 (m, 3H); 4.2–4.5 (m, 1H); 6.58 (s, 2H); 6.65–6.8 (m, 1H); 6.8–7 (m, 2H); 7–7.2 (m, 3H); 7.2–7.5 (m, 1H); 8–13 (m, 2H).

EXAMPLE 62
N-Methyl-N-[1-[5-(2-methoxyphenoxy)penty]piperid-4-yl]-4H-3,1-benzothiazin-2-amine hydrogen fumarate (62).

Starting with 600 mg (2.3 mmol) of N-methyl-N-[4-piperidinyl]-4H-3,1-benzothiazin-2-amine and by condensing them with 630 mg (2.3 mmol) of 2-methoxy-1-(5-bromopentyloxy)-benzene according to the procedure of Example 16-3, the compound of formula 62 is prepared in a yield of 58%:

(62)

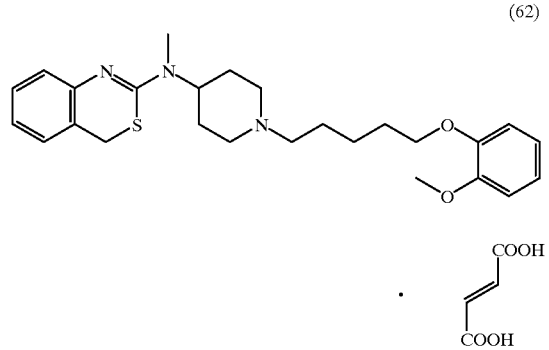

Empirical formula: $C_{30}H_{39}N_3O_6S$; Molecular mass: 569.72; Melting point: 175°; NMR (DMSO $d_6$) δ: 1.3–2.3 (m, 8H); 1.8–2.1 (m, 2H); 2.3–2.7 (m, 4H); 2.99 (s, 3H); 3.1–3.3 (m, 2H); 3.72 (s, 3H); 3.8–4 (m, 2H); 3.92 (s, 2H); 4.3–4.6 (m, 1H); 6.55 (s, 2H); 6.8–7 (m, 6H); 7–7.2 (m, 2H); 8–13 (m, 2H).

EXAMPLE 63
N-Methyl-N-[1-[2-(2-methoxyphenoxy) ethyl]piperid-4-yl]- 4H-3,1-benzothiazin-2-amine hydrogen fumarate (63).

Working as described in Example 16-3 starting with 600 mg (2.3 mmol) of N-methyl-N-[4-piperidinyl]-4H-3,1-benzothiazin-2-amine and 504 mg (2.3 mmol) of 2-methoxy-[1-(2-bromoethoxy)benzene, the compound of formula 63 is obtained in a yield of 63%:

(63)

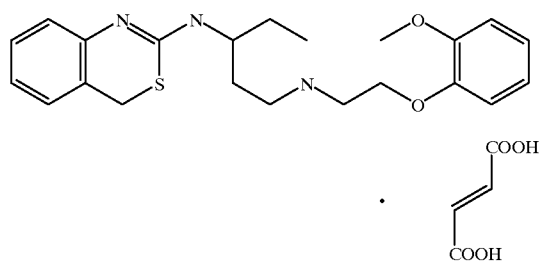

Empirical formula: $C_{27}H_{33}N_3O_6S$; Molecular mass: 527.64; Melting point: 178°; NMR (DMSO $d_6$) δ: 1.5–1.7 (m, 2H); 1.7–2 (m, 2H); 2.25 (t, 2H); 2.79 (t, 2H); 3.02 (s, 3H); 3.05–3.2 (m, 2H); 3.75 (s, 3H); 3.94 (s, 2H); 4.07 (t, 2H); 4.25–4.5 (m, 1H); 6.6 (s, 2H); 7.3–7 (m, 6H); 7.05–7.25 (m, 2H); 8–12 (m, 2H).

We claim:

1. N-heterocyclyl-1-aryloxyalkyl-4-piperidinamines selected from those of formula I (I)

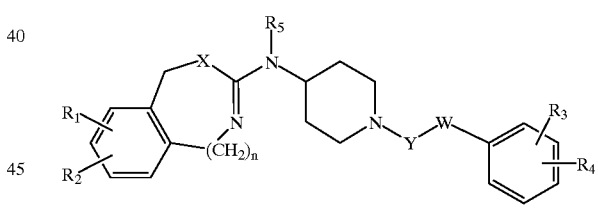

in which the substituents are defined as follows:
$R_1$ to $R_4$, which may be identical or different, represent:
  hydrogen
  branched or unbranched alkyl containing 1 to 4 carbon atoms
  branched or unbranched alkyloxy containing 1 to 4 carbon atoms
  halogen
  nitro
  hydroxyl
  trifluoromethyl or trifluoromethoxy,
$R_5$ represents:
  hydrogen
  branched or unbranched alkyl containing 1 to 6 carbon atoms
  branched or unbranched phenylalkyl containing 7 to 12 carbons, which can be substituted on the phenyl with one or two radicals defined as $R_1$,
W and X represent:

oxygen or sulfur,

Y represents:
polymethylene group containing 2 to 6 carbon atoms, or

—CH$_2$—CH(OH)—CH$_2$— n is 0, when the compounds contain an asymmetric carbon, in the form of their racemic mixtures or the pure enantiomers or mixtures thereof, and in any case therapeutically-acceptable inorganic or organic salts and hydrates thereof.

2. Compound according to claim 1, chosen from the following compounds:

N-methyl-N-[1-[4-(4-fluorophenoxy)butyl]piperid-4-yl]-4H-3,1-benzothiazin-2-amine hydrogen maleate N-methyl-N-[1-[3-(4-fluorophenoxy)propyl]piperid-4-yl]-4H-3,1-benzothiazin-2-amine hydrogen maleate N-methyl-N-[1-[2-(4-fluorophenoxy)ethyl]piperid-4-yl]-4H-3,1-benzothiazin-2-amine hydrogen maleate N-[1-[4-(4-fluorophenoxy)butyl]piperid-4-yl]-4H-3,1-benzothiazin-2-amine hydrogen maleate N-[1-[3-(4-fluorophenoxy)propyl]piperid-4-yl]-4H-3,1-benzothiazin-2-amine hydrogen maleate monohydrate N-ethyl-N-[1-[3-(4-fluorophenoxy)propyl]piperid-4-yl]-4H-3,1-benzothiazin-2-amine hydrogen fumarate N-benzyl-N-[1-[3-(4-fluorophenoxy)propyl]piperid-4-yl]-4H-3,1-benzothiazin-2-amine hydrogen maleate 6-fluoro-N-methyl-N-[1-[4-(4-fluorophenoxy)butyl]-piperid-4-yl]-4H-3,1-benzothiazin-2-amine hydrogen maleate 6-chloro-N-methyl-N-[1-[3-(4-fluorophenoxy)propyl]-piperid-4-yl]-4H-3,1-benzothiazin-2-amine hydrogen maleate 6-methoxy-N-methyl-N-[1-[3-(4-fluorophenoxy)propyl]-piperid-4-yl]-4H-3,1-benzothiazin-2-amine dihydrogen maleate N-methyl-N-[1-[4-(3,4-difluorophenoxy)butyl]piperid-4-yl]-4H-3,1-benzothiazin-2-amine hydrogen maleate N-[1-[4-(3,4-difluorophenoxy)butyl]piperid-4-yell-4H-3,1-benzothiazin-2-amine hydrogen maleate N-[1-[4-(4-chlorophenoxy)butyl]piperid-4-yl]-4H-3,1-benzothiazin-2-amine hydrogen maleate N-[1-[2-hydroxy-3-(4-fluorophenoxy)propyl]piperid-4-yl]-4H-3,1-benzothiazin-2-amine dihydrochloride hemi-hydrate N-[1-[2-hydroxy-3-(4-fluorophenoxy)propyl]piperid-4-yl]-4H-3,1-benzothiazin-2-amine N-methyl-N-[1-[2-hydroxy-3-(4-fluorophenoxy)propyl]-piperid-4-yl]-4H-3,1-benzothiazin-2-amine dihydrochloride N-methyl-N-[1-(4-phenoxybutyl)piperid-4-yl]-4H-3,1-benzothiazin-2-amine hydrogen maleate N-[1-[4-(4-fluorophenoxy)butyl]piperid-4-yl]-4H-3,1-benzothiazin-2-amine 6,7-dimethoxy-N-[1-[3-(3,4-difluorophenoxy)propyl]-piperid-4-yl]-4H-3,1-benzothiazin-2-amine dihydrogen maleate 6,7-dimethoxy-N-methyl-N-[1-[3-(3,4-difluorophenoxy)-propyl]piperid-4-yl]-4H-3, 1-benzothiazin-2-amine dihydrogen maleate 6-methyl-N-[1-[3-(3,4-difluorophenoxy)propyl]piperid-4-yl]-3,1-benzothiazin-2-amine hemifumarate N-methyl-N-[1-[4-(4-methylphenoxy)butyl]piperid-4-yl]-4H-3,1-benzothiazin-2-amine hydrogen maleate N-methyl-N-[1-[4-(4-methoxyphenoxy)butyl]piperid-4-yl]-4H-3,1-benzothiazin-2-amine hydrogen maleate N-[1-[2-hydroxy-3-(3,4-difluorophenoxy)propyl]piperid-4-yl]-4H-3,1-benzothiazin-2-amine dihydrochloride N-[1-[2-hydroxy-3-(3,4-difluorophenoxy)propyl]piperid-4-yl]-4H-3,1-benzothiazin-2-amine 6,7-dimethoxy-N-[1-[3-(4-fluorophenoxy)propyl] piperid-4-yl]-4H-3,1-benzothiazin-2-amine hemifumarate N-[1-[4-(4-fluorophenoxy)butyl]piperid-4-yl]-4H-3,1-benzoxazin-2-amine dihydrochloride 6,7-dimethoxy-N-[1-[4-(4-fluorophenoxy)butyl]piperid-4-yl]-4H-3,1-benzothiazin-2-amine hemifumarate 6-methyl-N-[1-[4-(4-fluorophenoxy)butyl]piperid-4-yl]-4H-3,1-benzothiazin-2-amine dihydrochloride hemihydrate N,6-dimethyl-N-[1-[4-(4-fluorophenoxy)butyl]piperid-4-yl]-4H-3,1-benzothiazin-2-amine hydrogen maleate (d1)-N-methyl-N-[1-[2-hydroxy-3-(3,4-difluorophenoxy)-propyl]piperid-4-yl]-4H-3,1-benzothiazin-3-amine dihydrochloride.

(S)-N-methyl-N-[1-[2-hydroxy-3-(3,4-difluorophenoxy)-propyl]piperid-4-yl]-4H-3,1-benzothiazin-2-amine hydrogen maleate N-methyl-N-[1-[4-(4-fluorophenylthio)butyl]piperid-4-yl]-4H-3,1-benzothiazin-2-amine hydrogen maleate N-methyl-N-[1-[5-(4-fluorophenoxy)pentyl]piperid-4-yl]-4H-3,1-benzothiazin-2-amine hydrogen fumarate N-methyl-N-[1-[3-(4-fluorophenoxy)propyl]piperid-4-yl]-4H-3,1-benzothiazin-2-amine hydrogen fumarate N-methyl-N-[1-[6-(4-fluorophenoxy)hexyl]piperid-4-yl]-4H-3,1-benzothiazin-2-amine hydrogen fumarate N-methyl-N-[1-[4-(3,4-dimethoxyphenoxy)butyl] piperid-4-yl]-4H-3,1-benzothiazin-2-amine hydrogen fumarate N-methyl-N-[1-[4-(2-methoxyphenoxy)butyl]piperid-4-yl]-4H-3,1-benzothiazin-2-amine hydrogen fumarate N-methyl-N-[1-[4-(2,3-dimethoxyphenoxy)butyl] piperid-4-yl]-4H-3,1-benzothiazin-2-amine hydrogen fumarate N-methyl-N-[1-[4-(3,5-dimethoxyphenoxy)butyl] piperid-4-yl]-4H-3,1-benzothiazin-2-amine hydrogen fumarate N-methyl-N-[1-[4-(2,6-dimethoxyphenoxy)butyl] piperid-4-yl]-4H-3,1-benzothiazin-2-amine hydrogen fumarate N-methyl-N-[1-[4-(2,6-difluorophenoxy)butyl]piperid-4-yl]-4H-3,1-benzothiazin-2-amine hydrogen fumarate N-methyl-N-[1-[5-(3,4-difluorophenoxy)pentyl]piperid-4-yl]-4H-3,1-benzothiazin-2-amine hydrogen fumarate N-methyl-N-[1-[4-(3,5-difluorophenoxy)butyl]piperid-4-yl]-4H-3,1-benzothiazin-2-amine hydrogen fumarate N-methyl-N-[1-[4-(2,4-difluorophenoxy)butyl]piperid-4-yl]-4H-3,1-benzothiazin-2-amine hydrogen fumarate N-methyl-N-[1-[4-(2,5-difluorophenoxy)butyl]piperid-4-yl]-4H-3,1-benzothiazin-2-amine hydrogen fumarate N-methyl-N-[1-[4-(3-fluoro-4-chlorophenoxy)butyl]-piperid-4-yl]-4H-3,1-benzothiazin-2-amine hydrogen fumarate N-methyl-N-[1-[4-(2,3-difluorophenoxy)butyl]piperid-4-yl]-4H-3,1-benzothiazin-2-amine hydrogen fumarate N-methyl-N-[1-[4-(3-chloro-4-fluorophenoxy)butyl]-piperid-4-yl]-4H-3,1-benzothiazin-2-amine hydrogen fumarate N-methyl-N-[1-[4-(3-fluorophenoxy)butyl]piperid-4-yl]-4H-3,1-benzothiazin-2-amine hydrogen fumarate N-methyl-N-[1-[4-(3-methoxyphenoxy)butyl]piperid-4-yl]-4H-3,1-benzothiazin-2-amine hydrogen fumarate N-methyl-N-[1-[4-(2-fluorophenoxy)butyl]piperid-4-yl]-4H-3,1-benzothiazin-2-amine hydrogen fumarate N-methyl-N-[1-[4-(2-methoxy-4-chlorophenoxy)butyl]-piperid-4-yl]-4H-3,1-benzothiazin-2-amine hydrogen fumarate N-methyl-N-[1-[4-(4-chlorophenoxy)butyl]piperid-4-yl]-4H-3,1-benzothiazin-2-amine hydrogen fumarate N-methyl-N-[1-[5-(4-methoxyphenoxy)pentyl]piperid-4-yl]-4H-3,1-benzothiazin-2-amine hydrogen fumarate N-[1-[5-(3,4-difluorophenoxy)pentyl]piperid-4-yl]-4H-3,1-benzothiazin-2-amine dihydrogen fumarate N-[1-[5-(4-fluorophenoxy)pentyl]piperid-4-yl]-4H-3,1-benzothiazin-2-amine dihydrogen fumarate (R) -N-methyl-N-[1-[2-hydroxy-3-(3,4-difluorophenoxy)-propyl]piperid-4-yl]-4H-3,1-benzothiazin-2-amine hydrogen fumarate N-methyl-N-[1-[5-(2-methoxyphenoxy)pentyl]piperid-4-yl]-4H-3,1-benzothiazin-2-amine hydrogen fumarate N-methyl-N-[1-[2-(2-methoxyphenoxy) ethyl]piperid-4-yl]-4H-3,1-benzothiazin-2-amine hydrogen fumarate.

3. Process for the preparation of a compound of claim 1 with $R_5$=H and Y=$(CH_2)_m$, m being 2 to 6 characterized in that an orthoaminobenzyl alcohol of formula VIII is reacted with a

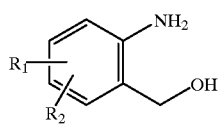
(VIII)

4-piperidyl iso(thio)cyanate of formula IXa in THF

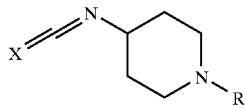
(IXa)

or dioxane as solvent, at a temperature of between 20 and 80° C., to give the intermediate hydroxymethyl(thio)urea Xa

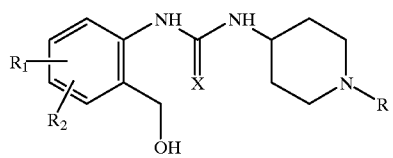
(Xa)

which is recovered by filtration and cyclized directly in concentrated hydrochloric acid at a temperature of between 20 and 80° C. to give the compound of general formula I where n=0.

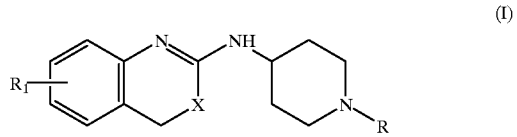
(I)

wherein the formulae VIII, IXa, Xa and I, the radicals $R_1$, $R_2$ and X have the same meanings as in claim 1 and R represents the group

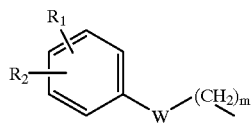

wherein $R_3$, $R_4$, and W have the same meanings as in claim 1 and m is 2 to 6.

4. Process for the preparation of a compound of claim 1 characterized in that an ortho-amino alcohol of formula (VIII) is reacted with an iso(thiocyanate) of formula (IXb) in THF or dioxane as solvent, at a temperature of

(VIII)

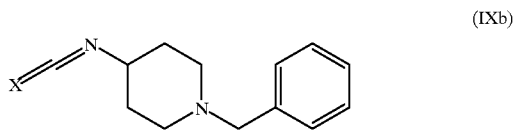
(IXb)

between 20 and 80° C. to give an intermediate hydroxymethyl-(thio)urea (Xb), which is recovered by filtration and which

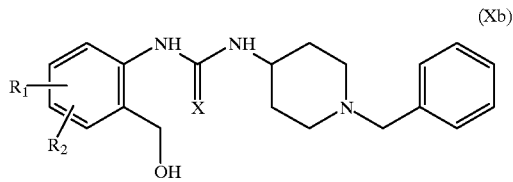
(Xb)

is cyclized directly by heating between 20 and 70° C. in concentrated hydrochloric acid to give the compound of formula XIb, which is then alkylated with a halide of formula $R_5$-Br

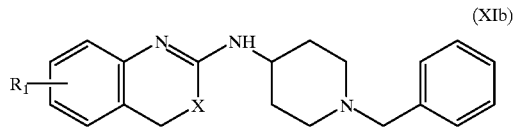
(XIb)

or $R_5$-I or a sulfate of formula $(R_5)_2SO_4$ in the presence of an alkaline carbonate or sodium hydride in DMF as solvent, to give the compound of formula (IVb), N-debenzylation of

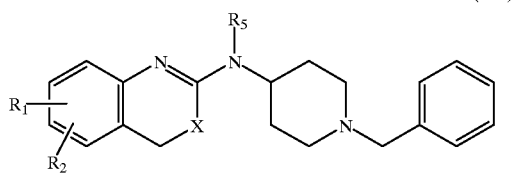
(IVb)

which IVb in the presence of α-chloroethyl chloroformate in methylene chloride followed by hydrolysis in refluxing methanol leads to the intermediate of formula (V), which

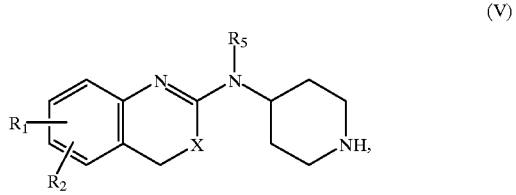
(V)

compound, on final N-alkylation with a halide of formula (VI) in DMF in the presence of 98/02 $K_2CO_3$/KI or a glycidyl ether of formula (VII) in methanol, gives the

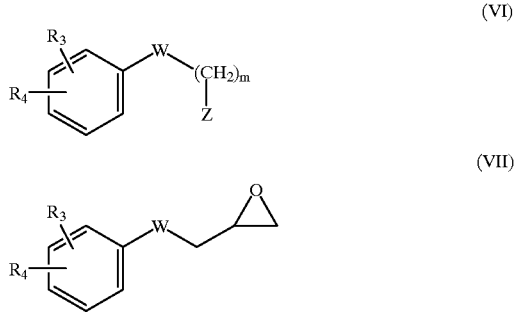
(VI)

(VII)

compound of general formula I of the present invention where n=0,

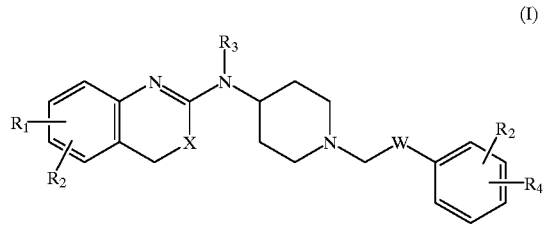
(I)

wherein the formulae IXb, Xb, XIb, IVb, V, VI, VII and I, the radicals $R_1$ to $R_5$, W, and X have the same meanings as in claim 1 and Z represents a bromine, chlorine or iodine atom and m can is 2 to 6.

5. Process for the preparation of a compound of claim 1 characterized in that a compound of formula I where $R_5$=H is reacted with an (aryl)alkyl halide $R_5Z$, wherein Z is Br, Cl, or I, or an alkyl sulfate $(R_5)_2SO_4$ in the presence of NaH or $Na_2CO_3$ to give the compound I where $R_5$ is other than H.

6. Pharmaceutical composition, characterized in that it contains, as active principle, at least one compound according to claim 1 combined with an inert pharmaceutical support or other pharmaceutically acceptable vehicle and which may or may not be combined with another active ingredient.

7. Method for the treatment of myocardial ischemia, including chronic stable angina, unstable angina and Prinzmetal's angina, silent ischemis, reinfarction, reocclusion and restenosis, comprising the step of administering to a patient suffering from such condition an effective amount of a compound of claim 1.

8. Method for the treatment of cerebral ischemia, strokes, transitory ischemic attacks, and neurodegenerative diseases, comprising the step of administering to a patient suffering from such condition an effective amount of a compound of claim 1.

9. Method for the treatment of atherosclerosis comprising the step of administering to a patient suffering from such condition an effective amount of a compound of claim 1.

10. Pharmaceutical composition, characterizd in that it contains, as active principle, at least one compound according to claim 2 combined with an inert pharmaceutical support or other pharmaceutically acceptable vehicle and which may or may not be combined with another active ingredient.

11. Method for the treatment of myocardial ischemia, including chronic stable angina, unstable angina and Prinzmetal's angina, silent ischemia, reinfarction, recclusion and restenosis, comprising the step of administering to a patient suffering from such condition an effective amount of a compound of claim 2.

12. Method for the treatment of cerebral ischemia, strokes, transitory ischemic attacks, and neurodegenerative diseases, comprising the step of administering to a patient suffering from such condition an effective amount of a compound of claim 2.

13. Method for the treatment of atherosclerosis, comprising the step of administering to a patient suffering from such condition an effective amount of a compound of claim 2.

* * * * *

UNITED STATES PATENT AND TRADEMARK OFFICE
CERTIFICATE OF CORRECTION

PATENT NO. : 6,011,032
DATED : Jan. 4, 2000
INVENTOR(S) : J.P. Rieu; J.F. Patoiseau; G. W. John; B. Legrand; J.P. Valentin It is certified that error appears in the above-indentified patent and that said Letters Patent is hereby corrected as shown below:

Column 3, line 32: In the formula (III), "$R_3$" should read -- $R_5$ --.

Column 3, line 42: In the formula (IV), "$R_3$" should read -- $R_5$ --.

Column 3, line 55: In the formula (V), "$R_3$" should read -- $R_5$ --.

Column 4, line 2: In the formula (I), "$R_3$" should read -- $R_5$ --.

Column 4, line 61: In the formula, "$CH_7$" should read "$CH_2$".

Column 5, line 2: "$R_3$" should read -- $R_5$ --.

Column 5, line 10: "$CH_7$" should read -- $CH_2$ --.

Column 5, line 15: "$R_3$" should read -- $R_5$ --.

Column 5, line 50: "$R_3$" should read -- $R_5$ --.

Column 5, line 57: "$R_3$" should read -- $R_5$ --.

UNITED STATES PATENT AND TRADEMARK OFFICE
CERTIFICATE OF CORRECTION

PATENT NO. : 6,011,032
DATED : Jan. 4, 2000
INVENTOR(S) : J.P. Rieu; J.F. Patoiseau; G. W. John; B. Legrand; J.P. Valentin It is certified that error appears in the above-indentified patent and that said Letters Patent is hereby corrected as shown below:

Column 6, line 2: "$R_3$" should read -- $R_5$ --.

Column 6, line 16: "$R_3$" should read -- $R_5$ --.

Column 7, line 27: "$(COO^{31})$:" should read -- $(\overline{COO})$ --.

Column 7, line 57: "160-1610°" should read -- 160-161° --

Column 7, line 58: "$(COO^{31})$:" should read -- $(COO^-)$: --.

Column 7, line 58: "NM(DMSO $d_6$)" should read: -- NMR(DMSO $d_6$) --.

Column 8, line 19: "$(COO^{31})$:" should read -- $(COO^-)$: --.

Column 8, line 51: "$(COO^{31})$:" should read -- $(COO^-)$: --.

Column 9, line 18: "$(COO^{31})$:" should read -- $(COO^-)$: --.

Column 10, line 21: "$(COO^{31})$:" should read -- $(COO^-)$: --.

UNITED STATES PATENT AND TRADEMARK OFFICE
CERTIFICATE OF CORRECTION

PATENT NO. : 6,011,032
DATED : Jan. 4, 2000
INVENTOR(S) : J.P. Rieu; J.F. Patoiseau; G. W. John; B. Legrand; J.P. Valentin It is certified that error appears in the above-indentified patent and that said Letters Patent is hereby corrected as shown below:

Column 10, line 53: "$(COO^{31})$:" should read -- $(COO^-)$: --.

Column 11, line 20: "$(COO^{31})$:" should read -- $(COO^-)$: --.

Column 11, line 51: "$(COO^{31})$:" should read -- $(COO^-)$: --.

Column 11, line 60: "armine" should read -- amine --.

Column 12, line 16: "$(COO^{31})$:" should read -- $(COO^-)$: --.

Column 12, line 46: "$(COO^{31})$:" should read -- $(COO^-)$: --.

Column 15, line 19: "4.85 (a,1H);" should read -- 4.85 (s,1H); --.

Column 16, line 21: "of a-chloroethyl" should read -- of α-chloroethyl".

Column 19, line 8: "$(COO^{31})$: should read: -- $(COO^-)$: --.

Column 22, line 42: "armine" should read -- amine --.

UNITED STATES PATENT AND TRADEMARK OFFICE
CERTIFICATE OF CORRECTION

PATENT NO. : 6,011,032
DATED : Jan. 4, 2000
INVENTOR(S) : J.P. Rieu; J.F. Patoiseau; G. W. John; B. Legrand; J.P. Valentin It is certified that error appears in the above-indentified patent and that said Letters Patent is hereby corrected as shown below:

Column 24, line 25: "121-1220;" should read -- 121-122° --.

Column 27, line 11: "(t,2A); should read -- (t,2H) --.

Column 27, line 13: "7.1-74(m,4H)" should read: -- 7.1-7.4(m,4H) --.

Column 28, line 25: At the end of the line, "1-[3-[4-" should read: -- 1-[3-(4- --.

Column 28, line 48: At the beginning of the line, "1-[1-[3-[4-" should read: -- 1-[1-[3-(4- --.

Column 28, line 49: At the end of the line, delete the "hyphen".

Column 31, line 51: At the beginning of the line, "yl)-" should read -- yl]- --.

Column 31, line 53: "piperid-4-yl)-" should read: -- piperid-4-yl]- --.

Column 34, line 4: "Phazmacol" should read: -- Pharmacol --.

UNITED STATES PATENT AND TRADEMARK OFFICE
CERTIFICATE OF CORRECTION

PATENT NO. : 6,011,032
DATED : Jan. 4, 2000
INVENTOR(S) : J.P. Rieu; J.F. Patoiseau; G. W. John; B. Legrand; J.P. Valentin It is certified that error appears in the above-indentified patent and that said Letters Patent is hereby corrected as shown below:

Column 35, line 36: "(S)-N-Methyl-N-E" should read:
-- (S)-N-Methyl-N- --.

Column 37, line 53: At the beginning of the line,
"4-yl-" should read -- 4-yl]- --.

Column 40, line 55: "66.65-6.85(m,1H);" should read:
-- 6.65-6.85(m,1H); --.

Column 43, line 6: "piperid-4-yl)-" should read:
-- piperid-4-yl]- --.

Column 49, line 3: The word "group" should be deleted.

Column 49, line 40: "piperid-4-yell-" should read:
-- piperid-4-yl]- --.

Column 52, line 9: At the beginning of the line,
"wherein" should read: -- wherein, in --.

UNITED STATES PATENT AND TRADEMARK OFFICE
CERTIFICATE OF CORRECTION

PATENT NO. : 6,011,032
DATED : Jan. 4, 2000
INVENTOR(S) : J.P. Rieu; J.F. Patoiseau; G. W. John; B. Legrand; J.P. Valentin It is certified that error appears in the above-indentified patent and that said Letters Patent is hereby corrected as shown below:

Column 52, line 15: In the formula, "$R_1$" should read -- $R_4$ -- and "$R_2$" should read: -- $R_3$ --.

Column 53, line 45: In the formula, "$R_3$" should read: -- $R_5$ -- and the second "$R_2$"(at the right side of the formula) should read -- $R_3$ --.

Column 53, line 54: At the beginning of the line, "wherein" should read -- wherein, in --.

Column 54, line 2: Delete the word "can".

Signed and Sealed this

Fourteenth Day of November, 2000

Attest:

Q. TODD DICKINSON

Attesting Officer

Director of Patents and Trademarks